(12) United States Patent
Gabay

(10) Patent No.: US 11,244,757 B1
(45) Date of Patent: Feb. 8, 2022

(54) COMPUTER-BASED ACCESS SECURITY AND VERIFICATION

(71) Applicant: FreedomCare, LLC, Queens, NY (US)

(72) Inventor: Yoel Gabay, Flushing, NY (US)

(73) Assignee: INNOVATE CARE LLC, New Hyde Park, NY (US)

( * ) Notice: Subject to any disclaimer, the term of this patent is extended or adjusted under 35 U.S.C. 154(b) by 243 days.

(21) Appl. No.: 16/294,535

(22) Filed: Mar. 6, 2019

Related U.S. Application Data

(63) Continuation-in-part of application No. 15/636,351, filed on Jun. 28, 2017, now Pat. No. 10,740,728.

(60) Provisional application No. 62/355,714, filed on Jun. 28, 2016.

(51) Int. Cl.
| | |
|---|---|
| *G16H 40/20* | (2018.01) |
| *G06Q 10/10* | (2012.01) |
| *H04L 29/06* | (2006.01) |
| *G06K 9/00* | (2006.01) |
| *G06F 16/61* | (2019.01) |

(52) U.S. Cl.
CPC ......... *G16H 40/20* (2018.01); *G06K 9/00228* (2013.01); *G06K 9/00288* (2013.01); *G06Q 10/1091* (2013.01); *H04L 63/083* (2013.01); *H04L 63/0861* (2013.01); *H04L 63/102* (2013.01); *H04L 63/107* (2013.01); *G06F 16/61* (2019.01)

(58) Field of Classification Search
None
See application file for complete search history.

(56) References Cited

U.S. PATENT DOCUMENTS

| | | | | |
|---|---|---|---|---|
| 2008/0114683 A1* | 5/2008 | Neveu | ..................... | G07C 9/257 705/50 |
| 2009/0204434 A1* | 8/2009 | Breazeale, Jr. | ........ | G06Q 30/04 705/3 |
| 2011/0082777 A1* | 4/2011 | Chess | ................ | G06Q 10/1091 705/32 |
| 2011/0209214 A1* | 8/2011 | Simske | .............. | G06K 9/00885 726/21 |
| 2013/0290154 A1* | 10/2013 | Cherry | ..................... | G07C 1/10 705/32 |
| 2015/0363745 A1* | 12/2015 | Hatch | ................. | G06Q 10/1091 705/32 |
| 2016/0217422 A1* | 7/2016 | Dujisin | .............. | G06Q 10/1091 |

FOREIGN PATENT DOCUMENTS

WO    WO-2014194939 A1 * 12/2014    ............... G07C 9/37

\* cited by examiner

*Primary Examiner* — Scott A Zare
(74) *Attorney, Agent, or Firm* — Leason Ellis LLP

(57) ABSTRACT

Computer-based access security includes executing secure login and authorization methodologies by which configuration parameters and permissions associated with a user at a user computing device are compared to database-stored respective configuration parameters and permissions associated with the user. Thereafter, the user is authorized or not to login and access mobile app functionality if the user successfully passes facial recognition and/or spoof detection techniques. Facial recognition techniques include collection and indexing of user captured photo as compared to already stored photo information pertaining to the user.

14 Claims, 22 Drawing Sheets

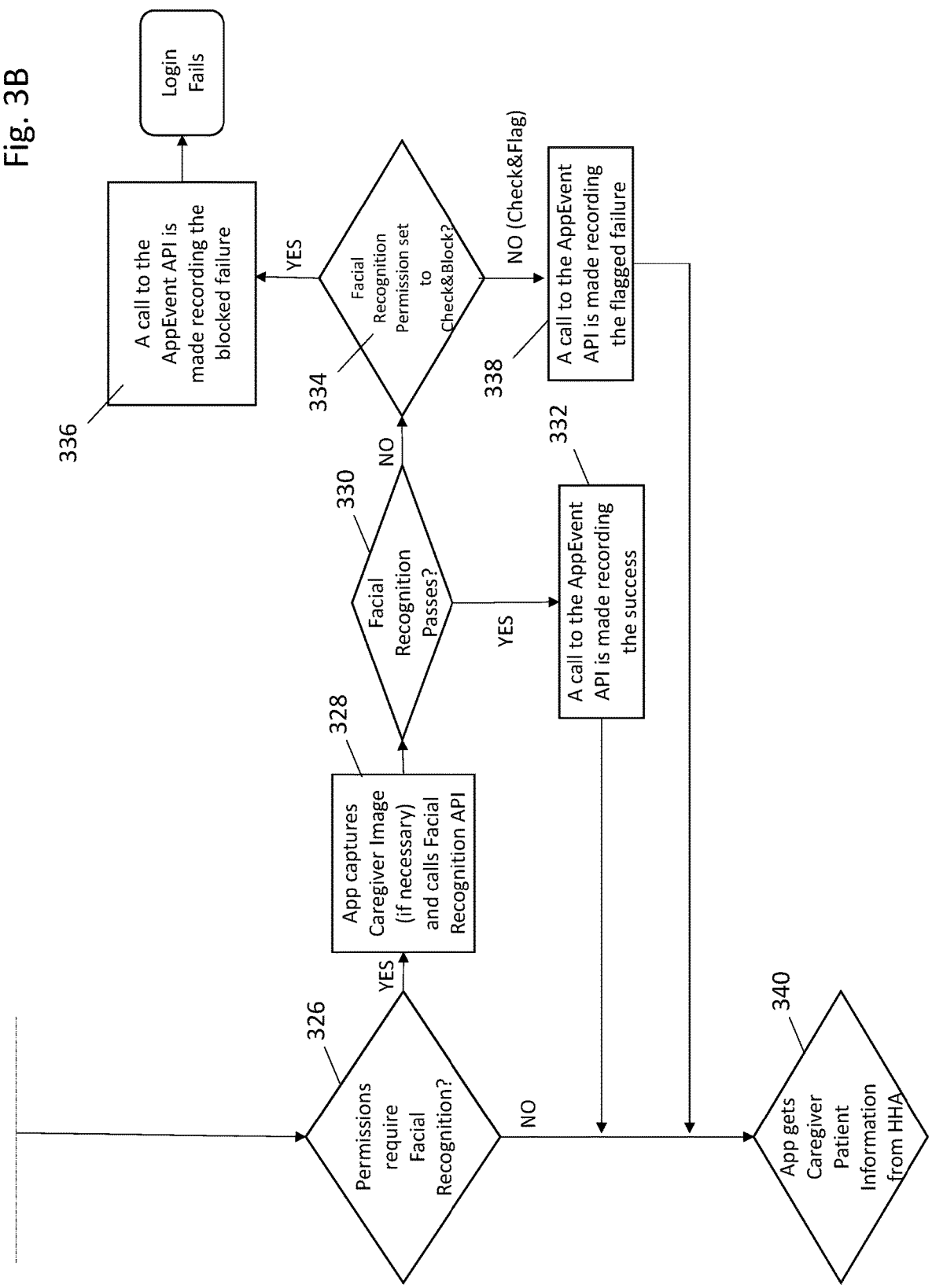

End of Week Timesheet

Week Ending 10/13/2018 (App version 1.93)

Employer Name: SSS Patient3
Employer ID #: 1625335
Employer Phone #: 888-555-0876

Assistant Name: SSS Caregiver2
Assistant ID #: 7589810 (code 1498)
Assistant Phone #:

| Day | Date | In | Out | Hours | In | Out | Hours | Total |
|---|---|---|---|---|---|---|---|---|
| Sunday | 10/07/2018 | 04:00 PM | 07:00 PM | 3.0 | | | | 3.0 |
| Monday | 10/08/2018 | 04:00 PM | 07:00 PM | 3.0 | | | | 3.0 |
| Tuesday | 10/09/2018 | 04:00 PM | 07:00 PM | 3.0 | | | | 3.0 |
| Wednesday | 10/10/2018 | 04:00 PM | 07:00 PM | 3.0 | | | | 3.0 |
| Thursday | 10/11/2018 | 04:00 PM | 07:00 PM | 3.0 | | | | 3.0 |
| Friday | 10/12/2018 | 04:00 PM | 07:00 PM | 3.0 | | | | 3.0 |
| Saturday | 10/13/2018 | | | | | | | |
| | | | | | | | Total: | 18.0 |

Risk Score: 50%

*Any times > 300 must have patient's name*

*Any times > 500 must have patient's name, patient's signature, patient's ...*

By signing this timesheet, Consumer and Personal Assistant both attest to the accuracy of the hours being reported as worked and that the Personal Assistant's schedule, as worked, was at the direction of the Consumer. I understand that Medicaid funds will be paid to the Personal Assistant on the basis of this timesheet. I understand that deliberately completing inaccurate time sheets can be fraud, which is a crime, and that severe penalties can be imposed for committing fraud.

Assistant's Signature

Employer's Signature

Employer Photo    Assistant Photo

Company Name: FreedomCare
Company Address: 1979 Marcus Ave, Suite C115, Lake Success, NY 11042
Company Phone: 718-386-3956
Company Fax: 718-989-3738
Company Email: info@freedomcareny.com All photos and signatures of employees and assistants were taken within 5 minutes of each other Followed Schedule %: 100%
Check In/Out %: 0%

FreedomCare

Live In End of Week Timesheet

Week Ending 11/24/2018 (App version 1.93)

Employer Name: SSS Patient4  
Employer ID #: 1625340  
Employer Phone #: 888-555-4321

Assistant Name: SSS Live#2  
Assistant ID #: 758918 (code 1500)  
Assistant Phone #:

| Day | Date | In | Out | Hours | In | Out | Hours | Total |
|---|---|---|---|---|---|---|---|---|
| Sunday | 11/18/2018 | | | | | | | |
| Monday | 11/19/2018 | | | | | | | |
| Tuesday | 11/20/2018 | 11:00 PM | 11:00 PM | 24.0 | | | | 13.0 |
| Wednesday | 11/21/2018 | 12:38 AM | 12:38 AM | 24.0 | | | | 13.0 |
| Thursday | 11/22/2018 | | | | | | | |
| Friday | 11/23/2018 | 08:00 AM | 08:00 AM | 24.0 | | | | 13.0 |
| Saturday | 11/24/2018 | 08:00 AM | 08:00 AM | 24.0 | | | | 13.0 |

Days > 13 hours: 0    Days who sleep break: 0    Days on call: 0    Total: 52.0

Key: Shift < SSS best have possible hours    Key: Sleep > SSS best have possible hours    Risk Score: 0%

Key: _____ no _____ possible hours

By signing this timesheet, Consumer and Personal Assistant both attest to the accuracy of the hours being reported as worked and that the Personal Assistant's schedule, as worked, was at the direction of the Consumer. I understand that Medicaid funds will be paid to the Personal Assistant on the basis of this timesheet. I understand that deliberately completing inaccurate time sheets can be fraud, which is a crime, and that severe penalties can be imposed for committing fraud.

Employer's Signature    Assistant's Signature    Followed Schedule %: 70%

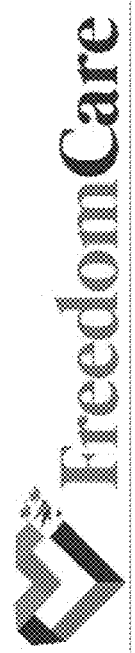

Clock In/Out %: 0%

Employer Photo    Assistant Photo

Company Name: FreedomCare  
Company Address: 1979 Marcus Ave, Suite C116, Lake Success, NY 11042  
Company Phone: 718-989-2856  
Company Fax: 718-989-9738  
Company Email: Info@FreedomCareNY.com All photos and signatures of employer and assistant have been taken within 5 minutes of each other

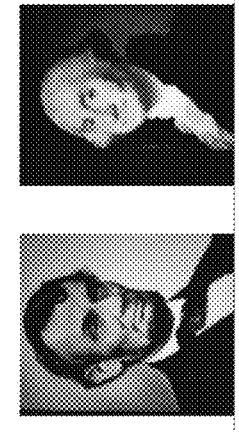

Fig. 15

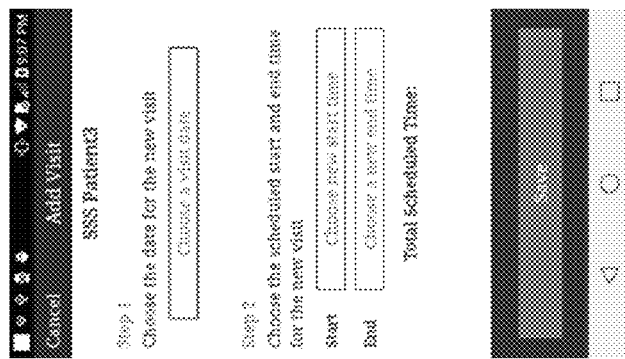
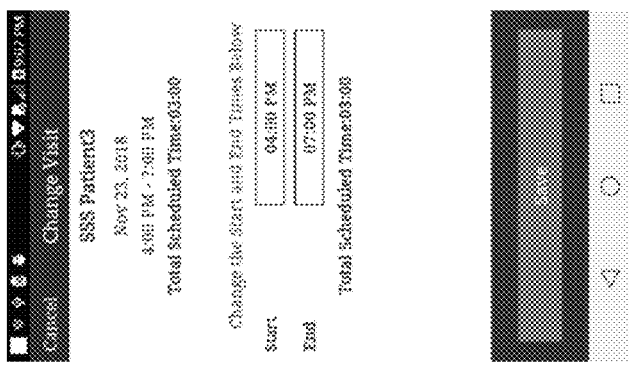
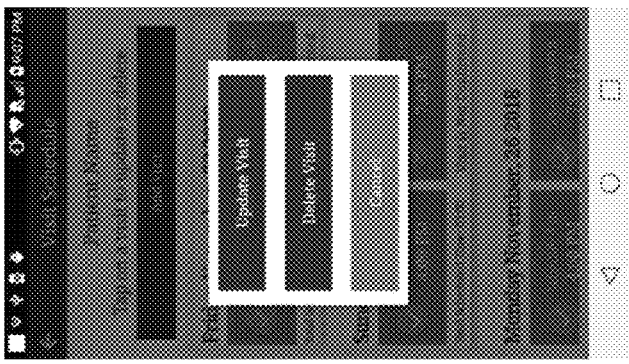
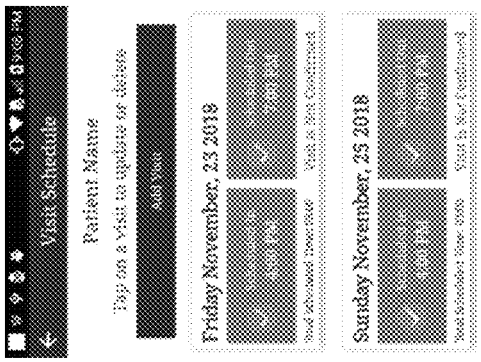
Fig. 20A   Fig. 20B   Fig. 20C   Fig. 20D

COMPUTER-BASED ACCESS SECURITY AND VERIFICATION

CROSS-REFERENCE TO RELATED APPLICATIONS

This application is a continuation-in-part of U.S. patent application Ser. No. 15/636,351, filed on Jun. 28, 2017, which claims priority to U.S. Provisional Patent Application Ser. No. 62/355,714, filed on Jun. 28, 2016, both of which are incorporated by reference as if expressly set forth in their respective entireties herein.

FIELD

The invention relates, generally, to security and metadata processing and, more specifically, to preventing fraud associated with attempts to falsify records.

BACKGROUND

The ability to confirm whether specific work services have been performed remains a challenge. Unscrupulous service providers have been known to falsify records, such as by forging signatures, and have been involved in efforts to be paid for work that was never completed.

Recently, consumer-directed homecare has increased, which has been helpful for consumers to direct their own care. For example, consumers and caregivers can work together to arrange for homecare, including with regard to scheduling work. Unfortunately, recording times and days worked by caregivers can be recorded and/or provided fraudulently. When undetected, timesheet fraud committed by home health care workers can result in billions of dollars of loss to insurance carriers and Medicaid. Such fraud is of utmost concern to many, including regulators, insurers, home health care providers and consumers.

BRIEF SUMMARY OF THE INVENTION

According to a broad aspect of the invention, systems and methods for authorizing user access to remote machines are provided. In one or more implementations, the method includes providing access to obtain information from a remote machine via a user computing device having a processor and a camera. The method performs these features by receiving, by the processor configured with the user computing device, one or more login credentials associated with a user. Next, the method verifies that the one or more login credentials are authorized to access the remote machine. In one or more implementations, verification of login credentials can include capturing a location of the user via GPS, comparing the captured location to the configuration information to determine whether the captured location is within a pre-determined tolerance, and thereafter granting access to the user to the remote machine if the captured location is within a pre-determined tolerance.

Once the user is verified, the method continues in one or more implementations by retrieving, by the processor, a list of configuration information from a database, the configuration information including one or more default configuration parameters and one or more permissions associated with the user. Thereafter, the method determines, by the processor, whether any of the one or more configuration items differ from the one or more default configuration parameters. If differences are found, the method replaces any respective differing default configuration parameter with the respective configuration item.

The method continues by capturing, via the camera at the computing device, a photo of the user. Next, the method collects and indexes the captured photo to transmit and store the captured photo to the database. Further, the method compares the captured photo to pre-existing photos stored in the database to determine a confidence score. Moreover, the method records the confidence score in the database and grants access to the user to the remote machine if the confidence score exceeds a predetermined threshold.

According to another broad aspect of the invention, in one or more implementations, a computer-based access security method for generating and transmitting a record representing a tracked time expended by a caregiver for services provided to a patient at a patient's location using a user computing device is provided. The method includes verifying, via location services, that the caregiver is within a set distance threshold from the patient's location. Then, the method captures, via a camera at the user computing device, a photo of the caregiver. Once captured, the method collects and indexes the captured photo to transmit and store the captured photo in a database. Next, the method compares the captured photo to pre-existing photos stored in the database to determine a confidence score. The confidence score is then recorded in the database. Thereafter, the user is granted access to the remote machine. The method in one or more implementations records the time of access in the database, and generates a timesheet representing the time of access. In one or more implementations, the timesheet is automatically transferred to a remote machine upon generation.

According to another implementation of the invention, a computer-based access security system for granting access to a remote machine by a user, the remote machine being in communication with a database, is provided. The system includes a user computing device having a camera. In one or more implementations, the user computing device is configured by a processor to receive at the user computing device, one or more login credentials associated with a user. The one or more login credentials are verified as whether they are authorized to access the remote machine.

Continuing with this aspect of the invention, in one or more implementations, the system is configured by the processor to retrieve, by the processor, a list of configuration information from the database, the configuration information including one or more default configuration parameters and one or more permissions associated with the user. Thereafter, the system determines, by the processor, whether any of the one or more configuration items differ from the one or more default configuration parameters. If any configuration items differ, the system replaces any respective differing default configuration parameter with the respective configuration item.

Continuing further with this aspect of the invention, in one or more implementations, the system is configured by the processor to capture, via the camera at the computing device, a photo of the user. Thereafter, the captured photo is collected and indexed to transmit and store the captured photo to the database. Next, the captured photo is compared to pre-existing photos stored in the database to determine a confidence score. This confidence score can be recorded in the database. In the event that the confidence score exceeds a predetermined threshold, the system grants access to the user to the remote machine.

According to still another aspect of the invention, a computer-based access security system for generating and transmitting a record to a database representing a tracked time expended by a caregiver for services provided to a patient at a patient's location, is provided. The system includes a user computing device having a camera in one or more implementations. In one or more implementations, the user computing device is configured by a processor to verify, via location services, that the caregiver is within a set distance threshold from the patient's location. Thereafter, the system captures, via a camera at the user computing device, a photo of the caregiver. Once captured, the captured photo is collected and indexed to transmit and store the captured photo in the database. The system is configured to compare the captured photo to pre-existing photos stored in the database to determine a confidence score. In one or more implementations, the confidence score is recorded in the database. Access to a remote machine is thereafter granted to the user. In one or more implementations, the time of user access is recorded in the database. Finally, a timesheet representing the time of access can be generated.

These and other aspects, features, and advantages can be appreciated from the accompanying description of certain implementations of the invention and the accompanying drawing figures and claims.

BRIEF DESCRIPTION OF THE DRAWINGS

FIGS. 3A-3B show a method flow of an example process for securely logging in to a caregiver/patient mobile app via facial spoof and facial recognition processes, in accordance with an implementation of the present application;

FIG. 14 is an example display screen comprising a generated timesheet for weekly patient visits, in accordance with an implementation of the present application;

FIG. 15 is an example display screen comprising a generated timesheet for weekly patient live-in visits, in accordance with an implementation of the present application;

FIGS. 20A-D are example display screens illustrating interactive graphical controls for adding or modifying patient visit information, in accordance with an implementation of the present application.

DETAILED DESCRIPTION OF THE INVENTION

By way of overview and introduction, a system and method in accordance with one or more aspects of the present application are configured to provide improved security measures and metadata. The present application enables authentication of approved users by a computing device to access caregiving verification features via photo-identification, facial recognition and geo-location techniques. Thereafter, the systems and methods herein generate and complete a timesheet that is transmitted electronically to one or more devices remote to the computing device. In this way, the present application provides security by layering a plurality of processes associated with receiving input from one or more devices to reduce and/or eliminate fraud associated with recording time associated with performed work, such as in connection with healthcare services. Moreover, the present application reduces overhead that would otherwise be needed for recording labor, such as via an electronic or paper timesheet.

In one or more implementations, the present application includes a plurality of modules that can be integrated in a distributed platform, such as a mobile software application executable on one or more computing devices. Such devices can include mobile computing devices, such as smartphones, that can operate to electronically verify that both a party providing and a party receiving services actually signed a timesheet for a provider, thus assisting to verify that the provider actually worked the hours indicated on the timesheet. As shown and described herein, the present application significantly reduces or completely eliminates the ability to forge a party's signature on a timesheet, such as by a provider of work services, and improves upon other flawed systems, such as phone-based timesheet systems, which can be inadequate for being prone to fraud and/or violate privacy laws or other concerns. Accordingly, the present application provides a labor recording system and method that electronically ensures that the respective services were performed, such as for a patient and by caregiver, by requiring that each is actually present at a time when respective signatures are entered on a timesheet.

Figure 1:
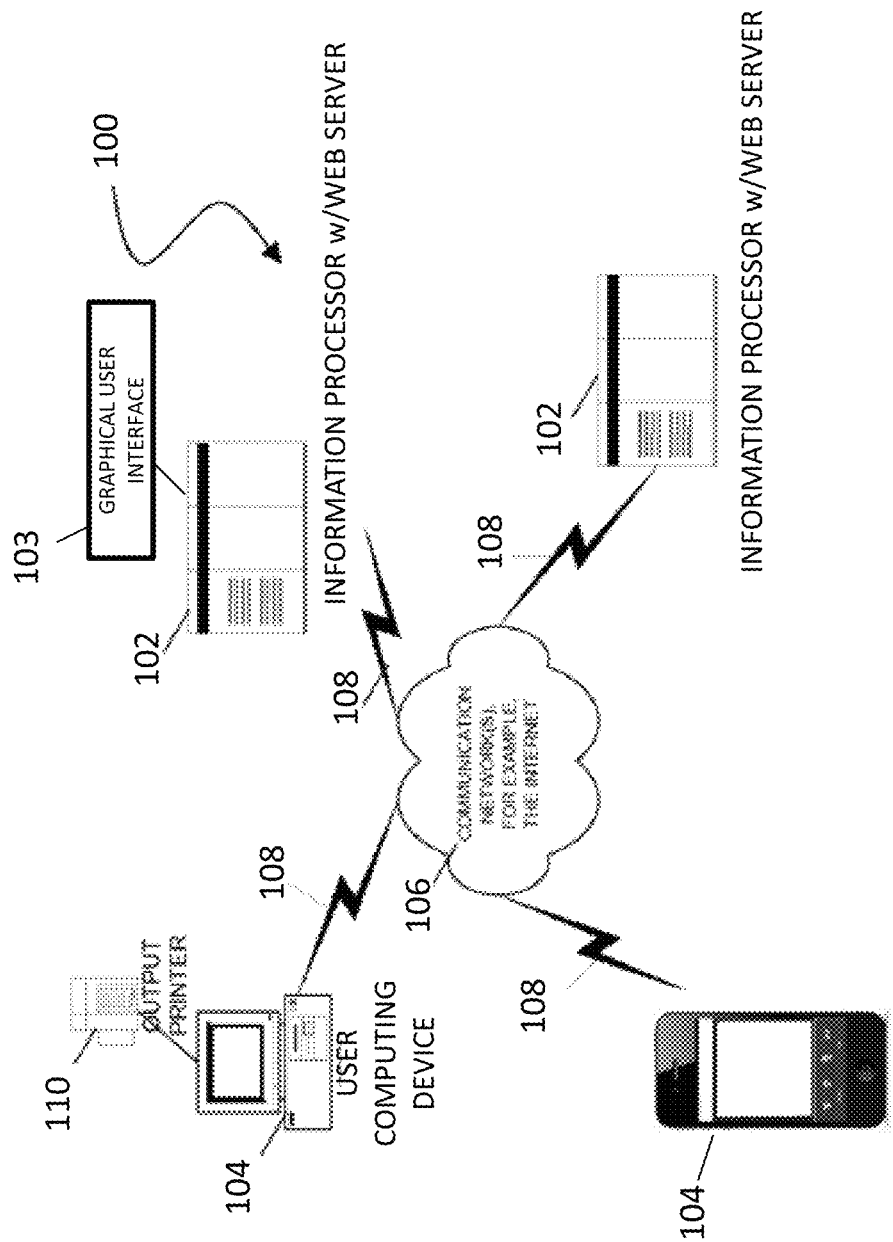
FIG. 1 is a diagram of an example hardware arrangement that operates for providing the systems and methods disclosed herein.

Referring now to the drawings in which like reference numerals refer to like elements, there is shown in FIG. 1 a diagram of an example hardware arrangement that operates for providing the systems and methods disclosed herein, and designated generally as system 100. The example system 100 is preferably comprised of one or more information processors 102 coupled to one or more user computing devices 104 across communication network 106. User computing devices 104 may include, for example, mobile computing devices such as tablet computing devices, smartphones, personal digital assistants or the like. Further, printed output is provided, for example, via output printers 110.

Information processor 102 preferably includes all necessary databases for the present invention, including image files, metadata and other information, such as relating to individuals, performance of services, or other relevant information. However, it is contemplated that information processor 102 can access any required databases via communication network 106 or any other communication network to which data processor 102 has access. Information processor 102 can communicate with devices comprising databases using any known communication method, including a direct serial, parallel, USB interface, or via a local or wide area network. Database(s) that are accessible by information processor 102 can contain and/or maintain various data items and elements that are utilized throughout the various operations of the system (100). For example, the database(s) can include user information, including account information concerning the user's various accounts third-party content and service providers. The database(s) can also include user preferences concerning operation of the system 100 and other settings related to the third-party content and service providers. By way of further example, the database(s) can also include a library of user computing devices 104, service providers and receivers of respective services. In one or more implementations, one or more databases can include datafiles representing specific signatures.

User computing devices 104 can communicate with information processor 102 using data connections 108, which are respectively coupled to communication network 106. Communication network 106 can be any communication network, but is typically the Internet or some other global computer network. Data connections 108 can be any known arrangement for accessing communication network 106, such as WiFi and Long-Term Evolution (LTE). In one or more implementations, dial-up serial line interface protocol/point-to-point protocol (SLIPP/PPP), integrated services digital network (ISDN), dedicated leased-line service, broadband (cable) access, frame relay, digital subscriber line (DSL), asynchronous transfer mode (ATM) or other access techniques are implemented.

User computing devices 104 preferably have the ability to send and receive data across communication network 106, and are equipped with web browsers to display the received data on display devices incorporated therewith. By way of example, user computing device 104 may be personal computers such as Intel Pentium-class computers or Apple Macintosh computers, but are not limited to such computers. Other computing devices which can communicate over a global computer network such as smartphones, tablets, personal digital assistants (PDAs) and mass-marketed Internet access devices can be used. In addition, the hardware arrangement of the present application supports devices that are connected via wired or wireless protocols via communication network 106.

System 100 preferably includes software that provides functionality described in greater detail herein, and preferably includes one or more information processors 102 and/or user computing devices 104 in communication with one another. One of the functions performed by information processor 102 is that of operating as a web server and/or a web site host. Information processor 102 typically communicates with communication network 106 across a permanent i.e., unswitched data connection 108. Permanent connectivity ensures that access to information processor 102 is always available.

Figure 2:
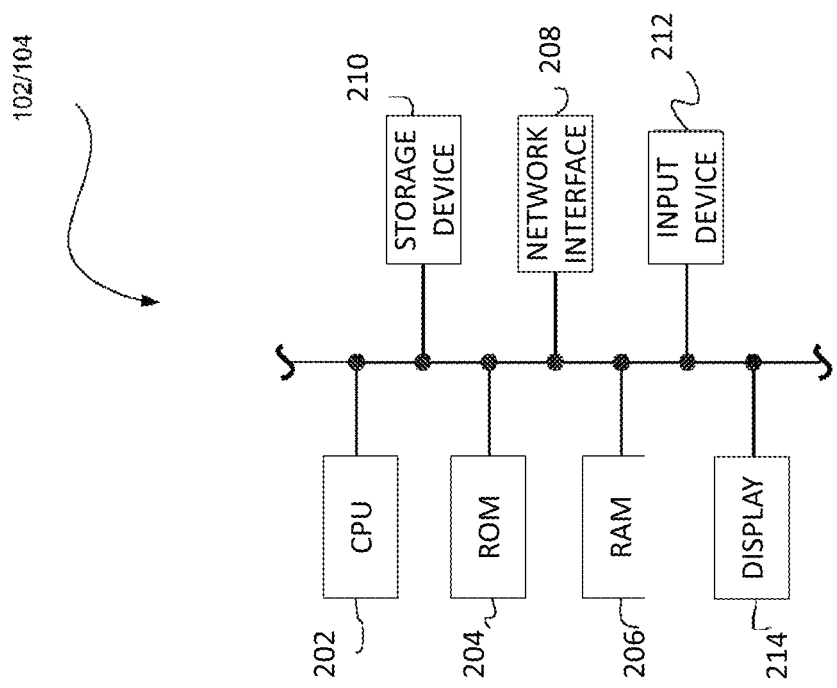
FIG. 2 is a block diagram that illustrates the functional elements of an information processor or user computing device, in accordance with an implementation of the present application.

As shown in FIG. 2 the functional elements of information processor 102 or user computing device 104, and preferably include one or more processors 202 used to execute software code in order to control the operation of information processor 102, read only memory (ROM) 204, random access memory (RAM) 206 or any other suitable volatile or non-volatile computer readable storage medium, which can be fixed or removable. FIG. 2 also includes one or more network interfaces 208 to transmit and receive data to and from other computing devices across a communication network. The network interface 208 can be any interface that enables communication between any of the devices (e.g., 102, 104) shown in FIG. 1 and includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting the devices and/or communication networks, such as private networks and the Internet. Such connections can include a wired connection or a wireless connection (e.g., using the IEEE 802.11 standard known in the relevant art) though it should be understood that network interface 208 can be practically any interface that enables communication to/from the processor 202.

Continuing with reference to FIG. 2, storage device(s) 210 can be included such as a hard disk drive, floppy disk drive, tape drive, CD-ROM or DVD drive, flash memory, rewritable optical disk, rewritable magnetic tape, or some combination of the above for storing program code, databases and application code. In certain implementations, memory 204, 206 and/or storage device(s) 210 are accessible by the processor 202, thereby enabling the processor 202 to receive and execute instructions stored on the memory 204, 206 and/or on the storage 210. Further, elements include one or more input devices 212 such as a keyboard, mouse, track ball and the like. Input device 212 can include other specialized hardware and/or software components, such as a camera, microphone or other captured devices. Moreover, display 214 can include a screen or any other such presentation device that enables the system to instruct or otherwise provide feedback to the user regarding the operation of the system (100). By way of example, display 214 can be a digital display such as an LCD display, a CRT, an LED display, or other such 2-dimensional display as would be understood by those skilled in the art. By way of further example, a user interface and the display 214 can be integrated into a touch screen display. Accordingly, the display is also used to show a graphical user interface, which can display various data and provide "forms" that include fields that allow for the entry of information by the user. Touching the touch screen at locations corresponding to the display of a graphical user interface allows the user to interact with the device to enter data, control functions, etc. So when the touch screen is touched, the interface communicates this change to processor, and settings can be changed or user entered information can be captured and stored in the memory.

One or more software modules can be encoded in the storage device(s) 210 and/or in the memory 204, 206. The software modules can comprise one or more software programs or applications having computer program code or a set of instructions executed in the processor 202. Such computer program code or instructions for carrying out operations or aspects of the systems and methods disclosed herein can be written in any combination of one or more programming languages, as would be understood by those skilled in the art. The program code can execute entirely on one computing device (e.g., information processor 102) as a stand-alone software package, partly on one device and partly on one or more remote computing devices, such as, a user computing device 104, or entirely on such remote computing devices. In the latter scenario and as noted herein, the various computing devices can be connected to the information processor 102 through any type of wired or wireless network, including a local area network (LAN) or a wide area network (WAN), or the connection can be made to an external computer (for example, through the Internet using an Internet Service Provider). It should be understood that in some illustrative implementations, one or more of the software modules can be downloaded over a network from another device or system via the network interface 208. For instance, program code stored in a computer readable storage device in a server can be downloaded over a network from the server to the storage 210.

It is to be appreciated that several of the logical operations described herein are implemented (1) as a sequence of computer implemented acts or program modules running on the various devices of the system 100 and/or (2) as interconnected machine logic circuits or circuit modules within the system (100). The actual implementation is a matter of design choice dependent on the requirements of the device (e.g., size, energy, consumption, performance, etc.). Accordingly, the logical operations described herein are referred to variously as operations, steps, structural devices, acts, or modules. As referenced above, the various operations, steps, structural devices, acts and modules can be implemented in software, in firmware, in special purpose digital logic, and any combination thereof. It should also be appreciated that more or fewer operations can be performed than shown in the figures and described herein. These operations can also be performed in a different order than those described herein.

Thus, the various components of information processor 102 need not be physically contained within the same chassis or even located in a single location. For example, as explained above with respect to databases which can reside on storage device 210, storage device 210 may be located at a site which is remote from the remaining elements of information processor 102, and may be connected to CPU 202 across communication network 106 via network interface 208.

The nature of the present application is such that one skilled in the art of writing computer executed code (software) can implement the described functions using one or more or a combination of popular computer programming languages including but not limited to C++, VISUAL BASIC, JAVA, ACTIVEX, HTML, XML, and ASP. The present application can also implement various known protocols such as SOAP and various known web application development environments. The present application can be implemented on various operating systems including, WINDOWS, MACOS, LINUX, IOS, ANDROID, or other known operating systems.

As used herein, references to displaying data on user computing device 104 refer to the process of communicating data to the computing device across communication network 106 and processing the data such that the data can be viewed on the user computing device 104 display 214 using a user interface displayed at the display, a web browser or the like. The display screens on user computing device 104 present areas within control allocation system 100 such that a user can proceed from area to area within the control allocation system 100 by selecting a desired interactive control object or button, textbox, or link. Therefore, each user's experience with control allocation system 100 will be based on the order with which (s)he progresses through the display screens. In other words, because the system is not completely hierarchical in its arrangement of display screens, users can proceed from area to area without the need to "backtrack" through a series of display screens. For that reason and unless stated otherwise, the following discussion is not intended to represent any sequential operation steps, but rather the discussion of the components of control allocation system 100.

While the present application provides systems and methods that are suitable for application to service providers generally, in one or more implementations, the present application is particularly well-suited for home healthcare services and is discussed in that context herein. A series of data entry, processing, and communication modules can be provided via a mobile application ("mobile app"), that can be installed on a worker's user computing device 104. The mobile app includes one or more software modules executing program code to permit a user, such as a home healthcare provider (or "caregiver"), on a daily basis, to electronically submit his or her timesheet for work performed, such as for a respective patient. The mobile app includes a touch-interactive user interface in which the user navigates through the interface by interacting with one or more interactive controls and objects displayed at the user interface by tapping them.

As shown and described herein, the present application provides enhanced security that assists in verifying that the provider is indeed performing his or her care for a specific patient. In particular, the present application provides a technical solution to the technical problem of verifying that the provider's identity, and verifying when and to what extent the provider has provided care. Current, conventional, techniques are susceptible to fraud, incompliance with timing recordation of clocking in/out, and timely submitting timesheets. The present application achieves these goals by implementing novel spoof detection and facial recognition techniques as applied to secure login and provider timesheet management technologies.

The secure login techniques contemplated herein include communication between a local computing device (e.g., user computing device 104) and one or more remote computing devices or servers (e.g., information processor 102) to exchange information associated with a user (e.g., a caregiver and/or a provider). The information exchanged includes criteria associated with the user that set forth the level and process of authorization necessary to permit the user to login. In one or more implementations, the information associated with the user is stored in records at a database at the information processor 102. In one or more implementations, the information associated with the user is stored as one or more confirmation items (e.g., configuration parameters or permissions described herein) that are exchanged between the local and remote computing devices via application programming interfaces (API) configured by the processor executing the mobile app on the computing devices. An API calls the information associated with the user from a data storage and compares it to the information provided by the user during the login process. Depending on the information input and the information called via API, the user is determined to be authorized or unauthorized to login.

Figure 3A:
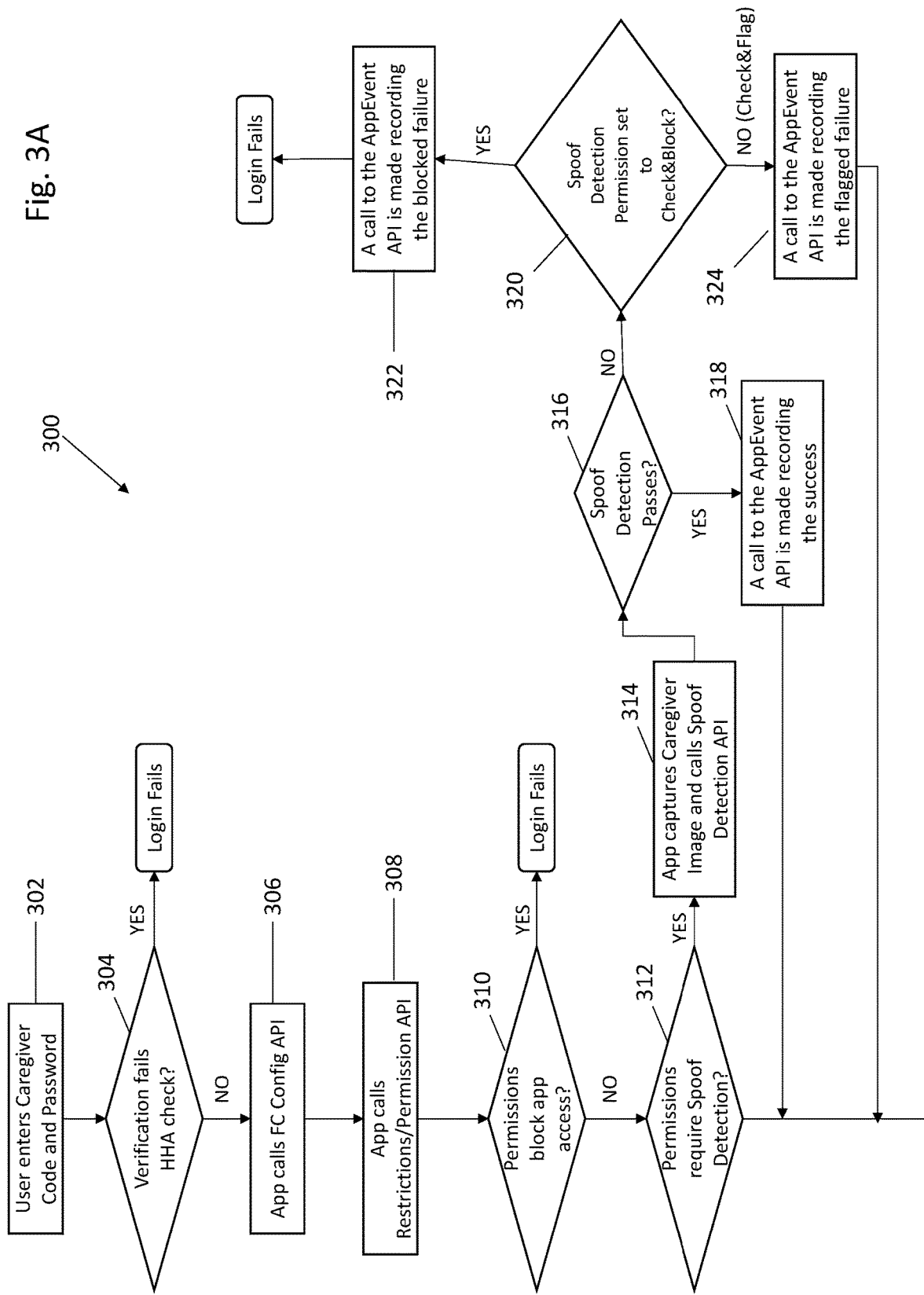
Figure 4:
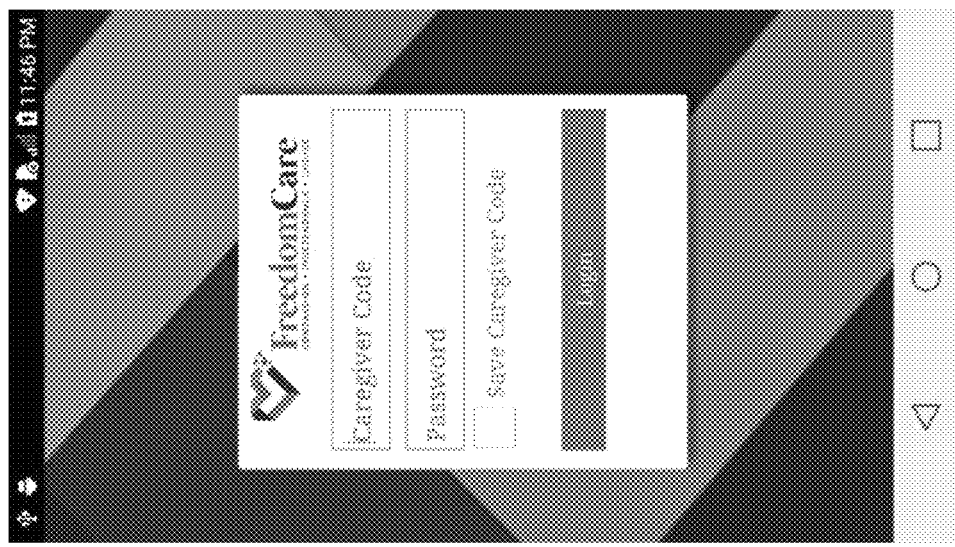
FIG. 4 is the example login entry display screen in accordance with an implementation of the present application.

With reference now to FIGS. 3A-3B, in one or more implementations, a secure login method 300 is described for logging into the mobile app. The method begins at step 302 in which a user (e.g., a service provider or caregiver) inputs one or more login credentials to the user computing device 104. In one or more implementations, the login credentials are compared to login credentials associated with the user that are stored from a remote information processor 102 for purposes of verifying the user's access to the mobile app. In some implementations, the remote information processor 102 transmits the login credentials associated with the user to the local user computing device 104 for comparison and verification. In other implementations, the input login credentials are transmitted to the remote information processor 102 and are compared remotely. The remote information processor can be a homecare software solution such as HHA Exchange. An example login screen for inputting login credentials is shown by FIG. 4. The login screen can include one or more interactive graphical screen controls that the user can interact with for inputting the login credentials. For example, login credentials can include a username, a code, a password, a PIN, or the like, and an option to save the login credentials for further use. Once the input login credentials and the login credentials previously associated with the user are received by a single device (e.g., the user computing device 104), the login credentials are verified by comparing the input login credentials to credentials stored in a database or a memory at the information processor that have been previously associated with the particular user, step 304. In implementations in which the login credentials are remotely verified, the remote information processor 102 transmits an approval to the user computing device 104. If the login credentials cannot be verified or no login credentials are associated with the user, the login process fails and the method 300 terminates.

If the login credentials are verified, thereafter the information processor 102 retrieves a list of configuration information associated with the user from a database. The configuration information specifies limit values (e.g., location distance limit) or values that control dynamic application processing. The configuration information includes one or more configuration parameters, step 306, and one or more permissions, step 308, each associated with the user. In one or more implementations, the configuration information is retrieved using an application programming interface (API) call between the user computing device 104 and information processor 102. The API call reviews the user input login credentials received at the information processor and determines whether any configuration information has been pre-set to be associated with the user. For example, configuration information can be pre-set to indicate that the user must be in a particular location to login, which is verifiable using location services such as GPS.

Continuing with respect to the configuration called by API, in one or more implementations, the configuration parameters and the permissions included in the configuration information are retrieved from the information processor in one or more API calls. Configuration parameters apply independent of who the user is, whereas permissions are user-specific. In one or more implementations, the configuration parameters and the permissions included in the configuration information are retrieved from the information processor in separate API calls. For example, the configuration parameters are called in a first API call, and in a second API call, information pertaining to the user-caregiver code can be provided as a look up identification and the second API call will either pass back specific configuration settings for that caregiver id or null indicating there is no current configuration information for that caregiver. The configuration information can be pre-set to be associated with particular users, though if no value is pre-set, or the user computing device 104 is unable to retrieve the particular configuration information from the database specific to the user the database includes default values which are retrieved. An example of a set of configuration information potentially associated with a user is shown below in Table 1. Such configuration information can include limits on what time a caregiver-user can login or clock in/out, what the minimum required mobile app version is, whether the user requires facial spoof detection or facial recognition to complete login or process patient visits, how much caregiver/patient history is associated with the user, and specific timeframes as to how long the mobile app will process actions before timing out.

TABLE 1

| Parameter | Description | Default Value |
| --- | --- | --- |
| GPSToleranceInFeet | If the distance away from the caregiver address is greater than this amount, the app will record the clock in or out as "out of bounds". | "300" |
| LateThresholdInMinutes | Number of minutes away from the schedule clock in or out time that the caregiver needs to initiate the clock in/out. If outside this range, it will be noted on the timesheet and with a warning dialog | "60" |
| LateScheduleThresholdInMinutes | Number of minutes away from the schedule clock in or out time that the caregiver needs to initiate the clock in/out. If outside this range, it will be recorded in the FC database | "15" |
| MinimumRequiredAppleVersion | Minimum app version for Apple/iOS. If the currently installed version of the app is lower, the app will warning the user and allow them to move to the Apple store to update. | N/A |
| MinimumRequiredAndroidVersion | Same as above for Android version of the app | N/A |
| FaceSpoof | Controls whether or not a "spoof detection" is performed on the face picture taken for face recognition. Check and Flag will record the failure in FC database but allow the app to continue while Check and Block will stop the login or timesheet from moving forward if this check fails. Values can be "DoNotCheck", "CheckAndFlagOnFailure" or "CheckAndBlockOnFailure" | "CheckAndFlagOnFailure" |
| FaceRecognition | Same as "FaceSpoof" above but applies to the actual call to compare the face picture to the one on record (i.e.. the face recognition check) | "CheckAndFlagOnFailure" |
| WeeksOfVisitHistory | During login the app retrieves previous weeks of visit information to check for unconfirmed visits. This value is how many weeks in the past for the app to read. The larger this number is, the longer the login time. | 4 |
| TrueFaceMinConfidenceLevel | The percentage of confidence returned from the spoof check before it is treated as a "pass" | 75% |
| FaceRecMinConfidenceLevel | The percentage of confidence returned from the face recognition check before it is treated as a "pass" | 75% |
| DefaultTimeoutTF | The number of seconds the app allows a spoof check to take before terminating it. A value of 0 equates to no timeout | 15 seconds |
| DefaultTimeoutFaceRec | The number of seconds the app allows the face recognition call to take before terminating it. A value of 0 equates to no timeout. | 15 seconds |

When retrieving the permissions via API call, if any permission retrieved includes the same identifying name as a configuration parameter, the value of that permission overwrites the value set by the configuration parameter. Permissions can include, for example, whether the user has access to the software on the user computing device 104, whether the user requires spoof detection or facial recognition techniques as additional layers of security to complete user login authentication, whether the user can initiate schedule changes, and other manually configurable mobile app options open to the user. An example of a set of permissions and default values potentially associated with a user is shown below in Table 2.

TABLE 2

| Parameter | Description | Default Value |
| --- | --- | --- |
| FaceSpoof | Same as and overrides the same named value from the general list | N/A |
| FaceRecognition | Same as and overrides the same named value from the general list. | N/A |
| ScheduleChanges | Controls whether or not this caregiver can initiate any schedule changes. Values are "YES" or "NO" | "YES" |
| WeeksOfVisitHistory | Same as and overrides the same named value from the general list | N/A |
| LockOutOfApp | If set to yes, does not allow the user to complete the login process (i.e., the specific caregiver cannot use the app). Values are "YES" or "NO" | "NO" |
| BlockManualConfs | Values are "YES" or "NO" | "NO" |

Thereafter, in one or more implementations, the method 300 continues by the processor of the user computing device 104 executing program code to evaluate and implement the set of permissions received from the information processor 102. In one or more implementations, evaluation of the user-associated permissions results in up to three determination being performed by the mobile app: (1) whether the user is authorized to access the service provider mobile app despite being authenticated by login credentials; (2) whether the user must pass spoof detection; and/or (3) whether the user must also pass facial recognition. Depending on the implementation, one, two, or three of these determinations are made in the method.

In the first of these three determinations of the method 300, as illustrated by the flow of FIGS. 3A-3B, the processor determines whether permissions block the user from accessing the service provider mobile app, step 310. For example, the processor evaluates the "LockOutOfApp" permission, a permission which determines if particular user login credentials should not provide access to the mobile app. The user login fails and access is denied in this example if the LockOutOfApp permission evaluates to YES. Otherwise, the method 300 continues and evaluates additional permissions associated with the user.

Continuing with this aspect of the method 300, in the second potential determination, the processor evaluates whether a permission evaluates to require spoof detection, step 312. Spoof detection is a technique in which an image is taken at the user computing device 104, and that image is evaluated by the mobile app to determine whether the image contains the face of a user. This includes checking whether a submitted photo is a photo of a face in a pre-existing photo—i.e., a determination whether a face in a photo was captured directly by the camera of the user computing device 104. In one or more implementations, spoof detection is performed using an API call. As an example, if the processor performs an API call to a TrueFace API, it thereafter evaluates the permissions set forth in a "FaceSpoof" permission. If the FaceSpoof permission returns "CheckAndFlagOnFailure", or "CheckAndBlockOnFailure" it results in an affirmative association to perform spoof detection on the user.

If spoof detection is determined by the permissions associated with the user, the method 300 branches to step 314, in which the processor at the user computing device 104 executes the spoof detection. In one or more implementations, spoof detection includes displaying a dialog to the user that explains that facial identification is required and the user must affirmatively interact with the user computing device 104 to proceed. In one or more optional implementations, the mobile app displays a check box that permits the user to check a "Don't show this again" option which will silence the dialog for future login, face spoof, or facial recognition attempts. The user may dismiss this dialog by, for example, tapping the dialog at user computing device 104. Thereafter, to perform spoof detection, a photo of the user is taken. In one or more implementations, the user computing device's camera function is invoked to take the photo of the user. To take the photo, the mobile first determines where a user's perceived face appears in a preview image provided by the camera lens when under operation. In one or more implementations, face detection is performed by drawing a square frame around what is perceived to be a user's face in the preview by analyzing the color/hue/lighting of the image. In such implementations, the frame enlarges as the user gets closer to the camera. In one or more implementations, the mobile app automatically captures the photo if the frame identifying a user face fills more than 75% of a preview area. In one or more implementations, the user must tap a button or portion of the display of the device to take a photo. The mobile app includes, in one or more implementations, a button or interactive prompt that permits toggling between front and rear facing cameras of the user computing device 104 to assist in capturing a user photo. In one or more implementations, the app will default to implementing the front facing camera if the user is identified by configuration information as a caregiver, and implementing the rear facing camera if the user is identified as a patient.

Once the photo is captured by the user computing device 104 at step 314, the method 300 continues to step 316 in which spoof detection is determined whether to be successful, indicating that a face appears in the captured image, and such face was not captured from a photo of another photo. In one or more implementations, spoof detection is performed by transmitting the captured photo to the information processor 102, whereby the captured photo is analyzed in view of the configuration parameters associated with the user as provided by the API call made if a permission indicates that spoof detection is to be performed for the particular logged in user.

In an example implementation, if the user configuration information includes a configuration parameter for "TrueFace", mobile app program code is executed to send the photo from the user computing device 104 to the information processor 102 to check the validity of the photo. Validity is performed by determining whether or not the captured photo is not a valid facial photo (i.e., to determine if it is a picture of a picture, rather than an original captured image). This check is skipped if the "FaceSpoof" configuration parameter has a value of "DoNotCheck". If the FaceSpoof has any other value, an evaluation of the image is performed to determine a confidence score between 0 and 1 as to how likely the captured photo is to be a photo of a face. This can be done by evaluating the color/hue/light and other photo properties of the captured image. The returned confidence score is determined to pass or fail facial spoof criteria based on a set confidence score established by other configuration parameters associated with the user. For example, the confidence score returned can be compared against a "TrueFaceMinConfidenceLevel" configuration parameter. If the confidence score suggests a success (e.g., greater than 0.75), the API call is recorded as a success, step 318. If the confidence score suggests a failure (e.g., less than 0.75) and the "FaceSpoof" configuration item is "CheckAndBlockOnFailure", step 320, the next check is not performed and further login or timesheet processing is stopped. In one or more implementations, an API call is made recording the blocked failure, step 322. In one or more implementations, the failed photo is recorded and stored, such as at the information processor 102 or a database. If the confidence score suggests a failure and another configuration item indicates that a failure should be flagged (e.g., if "FaceSpoof" is "CheckAndFlag"), an API call is made recording the flagged failure at the database record associated with the user, step 324. In one or more implementations, recording of successful, unsuccessful, or flagged facial spoof determinations occurs at a database of the information processor 102.

Continuing with the spoof detection methodology, if the spoof detection permission evaluates successfully, if a permission associated with the user evaluates to determine no spoof detection is required for that user, or if the spoof detection fails but evaluates to permit the user to continue but the failure is flagged (e.g., a "CheckAndFlag" result at step 324), the method 300 next evaluates whether the third potential permissions determination is implemented, namely whether a permission evaluates to require facial recognition, step 326. The method of performing facial recognition is similar to that of the facial spoof determination, except that the photo captured is transmitted to the remote information processor 102 to be compared to photos stored in databases or memories therein that are associated with the user, rather than evaluated at the user computing device 104. In one or more implementations, facial recognition is performed using a Face Recognition API. As an example, if the processor evaluates a permission "FaceRecognition" associated with the Face Recognition API to check and flag on a failure, or to check and block on a failure, the mobile app is instructed to have an affirmative association to perform facial detection on the user. If necessary, the method 300 captures a photo of the user using the on-board camera of the user computing device 104 in the same way as in the facial spoof determination, step 328.

Further to the third permissions determination of method 300, at step 330, the processor of the user computing device 104 determines whether facial recognition passes. Facial recognition passes when the photo captured by the on-board camera sufficiently matches a face photo stored in a database or memory of the information processor 102 that is associated with the user. To perform this comparison, the captured user photo is transmitted to a remote server via a collection and indexing function that stores the captured user photo for comparison to photos of the user stored at the information processor 102. In one or more implementations, collection and indexing includes collecting photos of patients and caregivers when first added to the system. The mobile app saves the pictures as full picture objects. Thereafter, an API call is made to add the photo to a collection. This is done by "indexing" the facial features and storing the metadata associated with the photo in the collection. To facilitate comparison of the collected photo to stored photos, the collection name at the remote server is set to match information associated with the user; for example, the caregiver's code or patient administration ID. Comparison includes comparing the color/hue/lighting and other image properties (e.g., facial features) of the respective photos to one another. The mobile app then makes a Face Recognition API call to search the face identified in the captured image against the images having caregiver/patient faces in the database of the information processor. In one or more implementations, the comparison search internally indexes the photo and compares the index information with the information identified in the collection function. The comparison returns either no match information if no face could be identified in the captured photo or a match with a confidence score indicating how close of a match was found to an image in the database.

Like the spoof check, the mobile app determines whether facial recognition passes or fails based on the confidence score as compared to the value in an associated configuration item (e.g., "FaceRecMinConfidenceLevel"). If the confidence score suggests a success, the API call records a success at the user computing device, the information processor, or both, step 322. If the confidence score suggests a failure, the method 300 determines whether there are any configuration parameters that indicate login authorization should cease upon failure of facial recognition, step 334. For example, if a "FaceRecognition" configuration parameter has a value of "CheckAndBlockOnFailure", further login or other processing is stopped. In one or more implementations, an API call is made recording the blocked failure at the user computing device, information processor, or both, step 336. In one or more implementations, the failed photo is recorded and stored, such as at the information processor 102 or a database In one or more implementations, if the confidence score suggests a failure and a configuration parameter has a value indicating that the comparison should be flagged due to a failure, an API call is made recording the flagged failure, step 338. In one or more implementations, recording of a flagged facial recognition determination occurs at the user computing device 104, a database of the information processor 102, or both.

Recordation of a facial spoof or facial recognition check result is performed to gather statistics on the effectiveness of the face recognition calls, i.e., that of the TrueFace API face spoof check and the Face Recognition API check. The app will record both calls as long as the call has been made (i.e., it will not record if the config item is "DoNotCheck") and will record success, a check failure (the API succeeds but states the check was not a match), a failure of the API call or a timeout. The call status is recorded anytime the API is called including during login and timesheet processing. A series of exemplary recordable parameters are shown below in Table 3.

TABLE 3

| Configuration Parameter | Recorded Information |
| --- | --- |
| Session ID | A unique number created each time user logs in |
| Provider | Either TrueFace or FaceRec |
| Service | Either Spoof or Recognition |
| EventType | Login |
| Result | Success, Flag, Block, or APICallFailed |
| ConfidenceScore | A number from 0 to 1 if the API call was successful |
| ForWho | Caregiver |
| ForWhoID | Caregiver ID |
| ErrorString | Only applicable if the API call fails |

If the facial recognition permission evaluates to not perform facial recognition (e.g., "DoNotCheck") at step 326, or if the facial recognition detection is successful at step 330, or fails but evaluates to merely flag the failure (e.g., "CheckAndFlag") at step 334, the method 300 completes authorization of the user by the information processor 102 to access the mobile app via the user computing device 104. For example, a caregiver user can be authenticated as a caregiver via the HHA Exchange, and authenticated to be authorized to provide services to one or more patients as identified by the HHA Exchange.

Upon successful login by the user to the mobile app, the user gains access to various functionality provided by the app. In one or more implementations, the mobile app reads in visit information associated with known patients of the user. This can be displayed and reviewed as described elsewhere herein.

Additionally, the mobile app can be configured to send/receive messages to the user from a third-party. In one or more implementations, the user is immediately prompted to review any unread messages upon login. Unread messages can include, for example, messages from patients, other caregivers, users, or the HHA Exchange. Unread messages are transmitted from information processor 102 to the user computing device 104 via the communication network 106. In one or more implementations, messages are stored in a database at the remote processor.

Figures 5A, 5B:
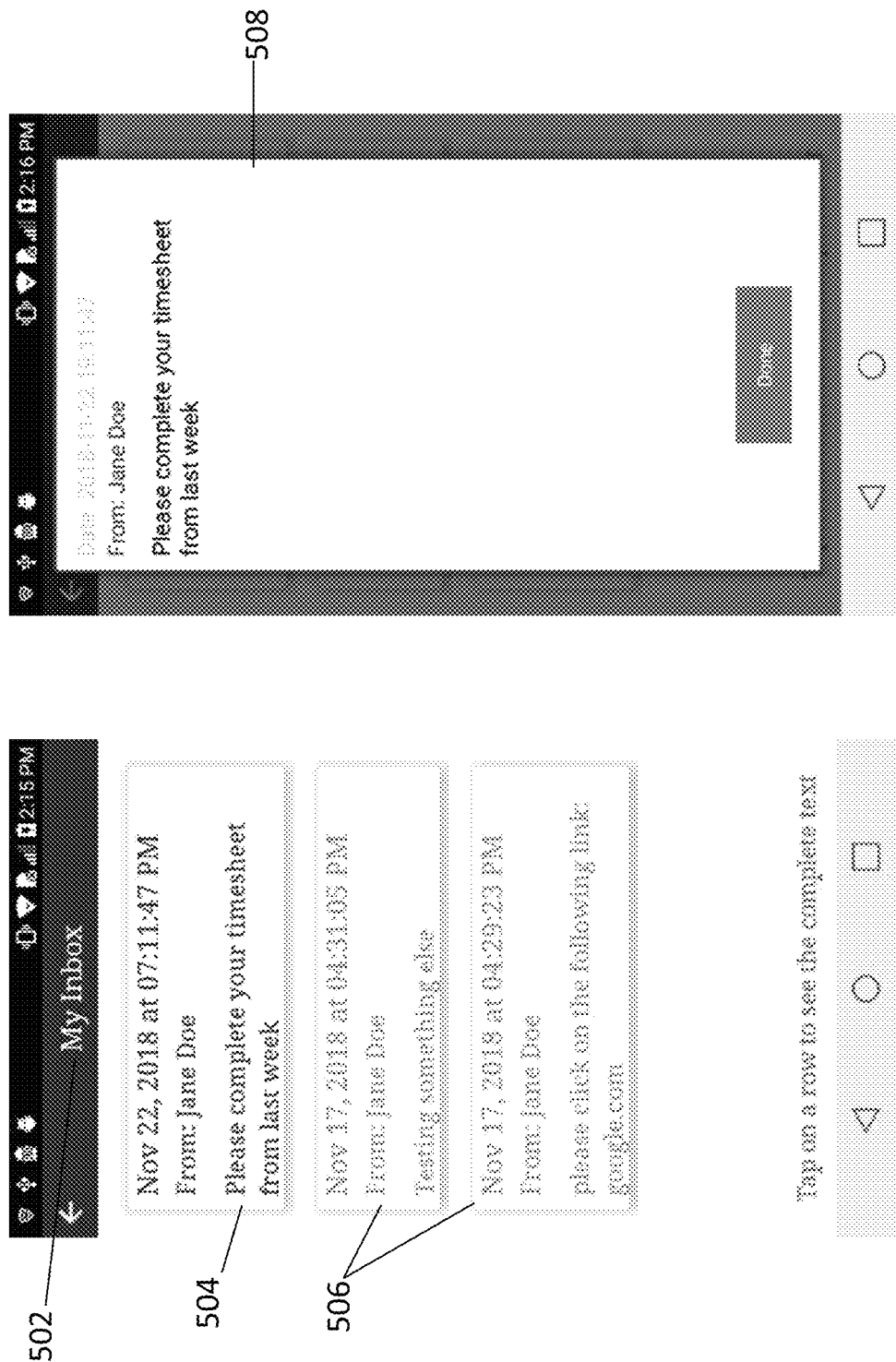
FIGS. 5A and 5B are examples of display screen displaying messages received by a user in accordance with an implementation of the present application.

Upon receipt at the user computing device 104, unread messages are displayed on a message list screen, which is described with more particularity with regard to FIGS. 5A-5B. In one or more implementations, unread messages are displayed in an inbox 502 at the message list screen. The inbox 502 displays a list of messages that have been sent to the authenticated and logged in user. In one or more implementations, the inbox 502 is sortable by the user. For example, the inbox 502 can be sorted from newest to oldest based on date created, alphabetically by to/from or the subject line, or by other categorizations, such as manual flagging of importance of the message. In one or more implementations, the unread messages 504 are shown in a first color (e.g., dark blue), and read messages 506 are shown in a second color (e.g., light gray). In one or more implementations, each row of the inbox 502 displays the message creation date, the name of the person who sent the message to the user and a few preview lines of the message text. To open a message, a user uses haptic feedback aspects of the user computing device 104 to physically tap an interface element representing the desired message to cause it be displayed at the user computing device for reading. For example, a tapped message will open into a window 508 that displays the text of the message. If the message contains more text than is displayable due to the resolution or visual constraints of the display of the user computing device 104, the device generates a scroll bar at the window 508 for the user to navigate through the remaining text.

In one or more implementations, the user must tap each unread message 504 before it can progress to additional functionality provided by the mobile app. In one or more implementations, the user is prevented from marking any unread messages 506 as read without opening the respective unread message. In one or more implementations, messages, whether unread or read, cannot be deleted from the user computing device 104. In such implementations, messages are stored at the remote information processor 102 and must be deleted directly from there.

Figure 6:
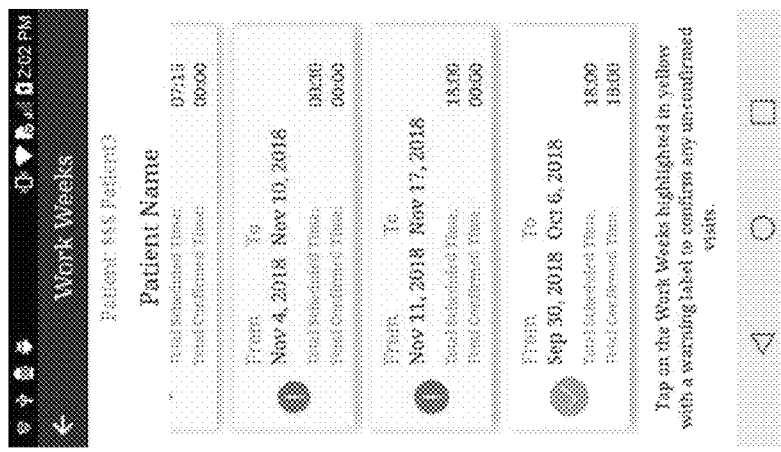
FIG. 6 is an example display screen comprising the confirmation status of patient visits, in accordance with an implementation of the present application.

Additionally, the mobile app can prompt a user to review his or her patient visits. This may be an automatic prompt in the case of which there are no unread messages, or the implementation permits the user to choose not to review the unread messages, or the user may be manually permitted to navigate to a patient review section via the interactive graphical controls of the mobile app. An example display screen showing unconfirmed and confirmed visits is illustrated by FIG. 6.

Patient visits can include both past and future patient visits. To view past visits, a user selects a particular patient history to view and taps an object at the mobile app, such as one that is displayed as "View Previous Weeks." When the patient is selected, the previous work week(s) pages are shown with any past week that has at least one visit. In one or more implementations, the number of past weeks read in during login is controlled by a configuration parameter.

Past visits also include confirmed and unconfirmed visits. The confirmed or not status of each visit, or each week of visits, depending on the implementation, is indicated by a warning symbol or a check mark. A visit with a check mark indicates that the visits have been confirmed by the user. Tapping a visit with a check mark will bring up a timesheet page with all the caregiving visits grouped in that overall visit (i.e., in the case of "weekly" visit groupings, described elsewhere herein) showing a green "confirmed" image stamped across the visit groupings. This is to allow a "read-only" view of the visits of a past week.

In one or more implementations, determining whether a user-caregiver has unconfirmed visits includes transmitting information regarding visit status associated with the user-caregiver from the remote information processor 102. Once the user computing device successfully receives visit data from the information processor 102, the user computing device 104 determines if there are any visits in the past that have not been "confirmed," that is, whether one or more previous provider visits have occurred without a clock out operation. In one or more implementations, confirming visits can be performed upon submission of a timesheet. In one or more implementations, if a caregiver has unconfirmed visits, the caregiver must resolve them before performing any future visits. In one or more other implementations, the caregiver can clock in/out future visits even if there are outstanding unconfirmed visits. If the weekly visit grouping has individual unconfirmed visits, in one or more implementations, a timesheet page is displayed to permit a user to review and confirm the specific visits prior to timesheet submission.

With regard to future visits, in one or more implementations, in addition to displaying the time and date of the future visit, the mobile app can include alarm and/or notification reminders as to the start and end times of a particular visit. For example, upon reading in a particular visit's information for a caregiver, the mobile app can create alarms to notify the user 15 minutes in advance of the next visit's start and end time. The alarm notification can be shown, for example, in the notification center of the user computing device 104 and if the user taps the notification, the mobile app is brought to the user's attention. In one or more implementations, a record of all pending alarms is stored at the user computing device 104 and is managed if the remote information processor 102 determines that there is a need to change the necessity or time of the alarm. For example, alarm changes can occur if a caregiver or patient schedule is changed, if a visit is started or ended before an alarm triggers, or if the phone is rebooted which requires all alarms to be reinstated.

Figure 7:
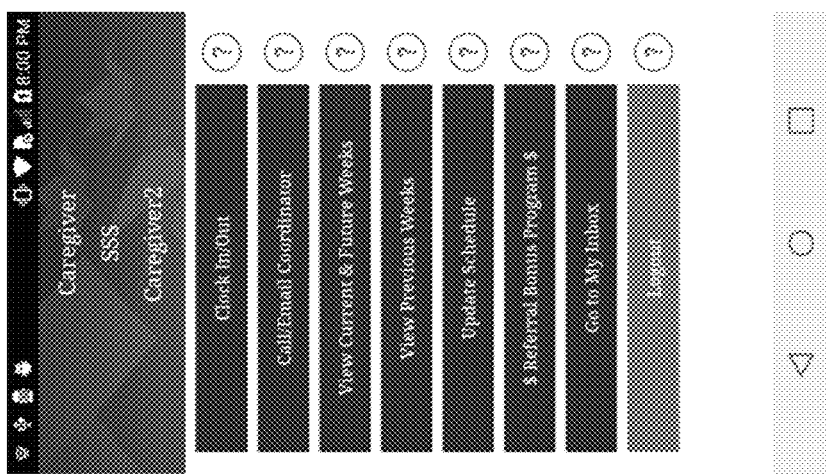
FIG. 7 is an example display screen illustrating selectable graphical screen controls at a home screen, in accordance with an implementation of the present application.

Once a user is successfully authorized and logged in, the user is displayed a home screen where many operations begin. In one or more implementations, the home screen provides interactive control objects for a user to access unread messages or review visit information. In one or more implementations, a user is prompted to review unconfirmed visits prior to displaying the home screen. An example home screen is illustrated in FIG. 7.

One advantageous functionality of the present application is a more secure way to verify and confirm the time spent by a caregiver with a patient. That is, the present application can perform secure clock in and clock out functions for patient visits. This functionality can be used in conjunction with timesheet generation functionality, described elsewhere herein.

Figure 8:
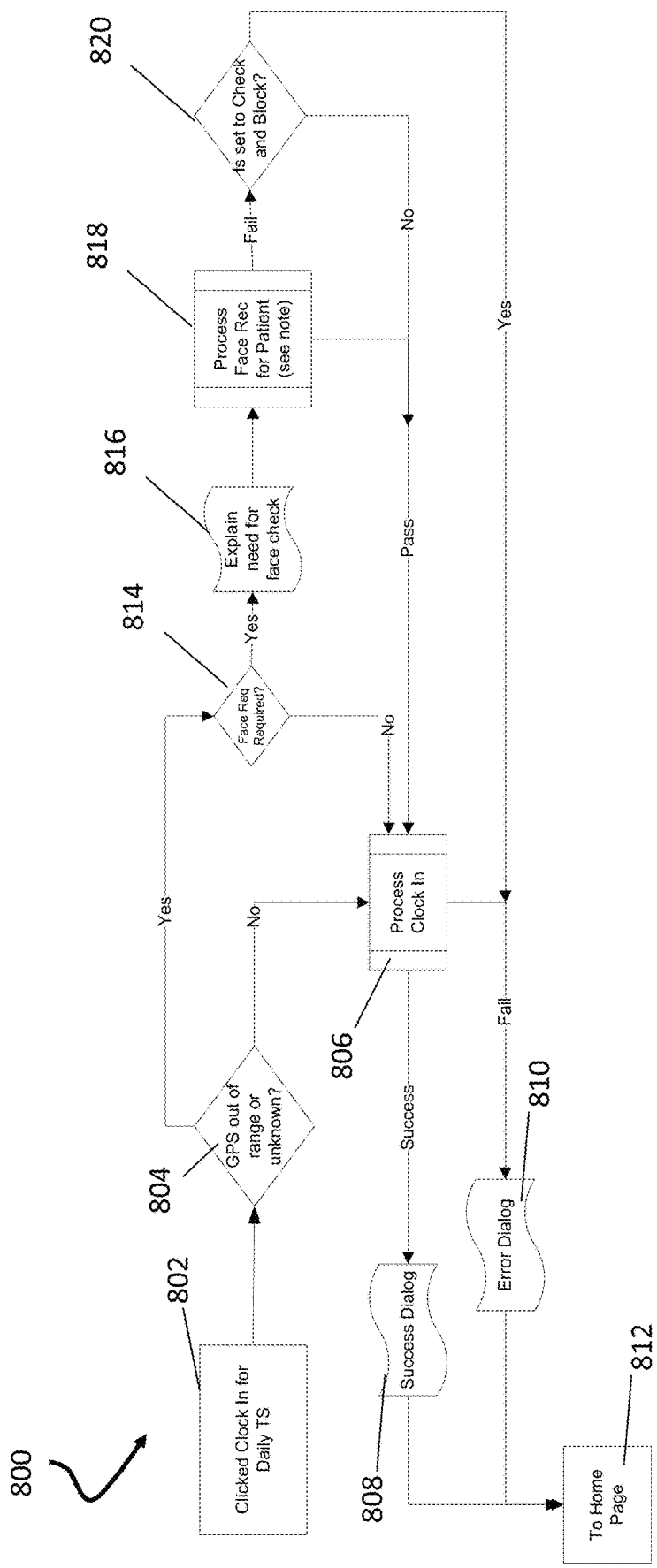
FIG. 8 is a method flow showing example caregiver "clock in" processes, in accordance with an implementation of the present application.

With reference now to FIG. 8, the present application provides a method 800 for a caregiver user to clock in a patient visit. The method 800 begins by a user selecting the "clock in/out" interactive control from the home screen of the mobile app, step 802. To confirm that the clock in or clock out is a legitimate action by a caregiver with respect to a patient visit, in one or more implementations, the caregiver and/or patient's current locations are determined. This location data is then checked against database records at the information processor 102 that indicate where the caregiver and patient are expected to be based on the expected care. Such location data can be recorded at the user computing device and/or information processor. If the current location data matches the stored visit location data in the database within a pre-determined tolerance, the clock in procedure can continue. In this way, the caregiver can be confirmed to be in the location where the particular patient was identified to be at for the visit by the information processor 102, step 804. In one or more implementations, the caregiver's location is checked using global position systems (GPS) built into the user computing device 104. Location checks can also include "higher accuracy" checks that add Network Positioning checks in addition to GPS to enhance user computing device positioning accuracy, as is known in the art. In one or more implementations, the location services check includes a mid-shift location check.

In this way, the mobile app can ensure that the caregiver is providing care to the patient throughout the duration of the visit, rather than just at the beginning and end of the visit. For example, the method 800 can set an alarm that will occur at roughly halfway through the duration of the visit after the caregiver clock in. In one or more implementations, the alarm will occur even if the app is not actively running. In one or more optional implementations, the alarm will generate a notification at the user computing device. If the visit is clocked in before the alarm is set to go off, the alarm is cancelled. When the alarm occurs, the user computing device 104 will retrieve the current position from the phone's location services and record the latitude, longitude and distance from the patient location. This location is checked with database records of the information processor 102. This additional clock in information can be recorded and passed to the information processor 102 servers as part of the clock in/out information recorded at time of visit confirmation.

If the caregiver's location is determined to be near to the patient's location within a pre-determined tolerance at time of clock in, or in implementations in which location services were not required, the method 800 branches to step 806 and processes the clock in. Processing of the clock in can include, for example, reviewing a permission associated with the caregiver and patient (e.g., an "EventType"), recording a timestamp of the clock in and confirming the visit. Additional detail regarding the processing of a clock in is described in U.S. patent application Ser. No. 15/636,351, which is incorporated by reference as set forth fully herein. If the clock in is processed correctly, a success dialog is displayed to the user, step 808. If the clock in process fails, an error dialog is displayed to the user, step 810. In either event, thereafter the method 800 returns the user to the home screen, step 812.

Continuing with this method flow, in the event that the caregiver's current location is determined to be outside of a prescribed threshold or range, or cannot be determined for other reasons (e.g., location services are turned off at the user computing device), the method branches to step 814, in which the mobile app at the user computing device 104 determines whether a facial recognition check on the patient is required. Facial recognition check determinations are performed as in method 300, except that if the caregiver's location is out of range or unable to be determined, the mobile app will perform a facial recognition check of the patient instead. For example, if the permission "FaceRecognition" associated with the caregiver returns a value of "DoNotCheck", no facial recognition is necessary and the method 800 branches to step 806 to process the clock in. If the permissions associated with the caregiver determine facial recognition is required, the method 800 branches to step 816 and the user computing device 104 displays a prompt explaining the need for a facial recognition check. The displayed prompt can include an affirmation that the user understands that his or her photo will be taken and stored with the information processor. Thereafter, facial recognition techniques are processed as described elsewhere herein, step 818. This includes checking the permissions associated with facial recognition, such as whether associated permissions are set to check for failed facial recognition to block clocking in for the visit, step 820. If the permissions do not include blocking clocking in for the caregiver or the facial recognition procedures are successful, the user computing device 104 processes the clock in. In alternative, or in addition, to facial recognition techniques, the method 800 can include facial spoof techniques as described elsewhere herein.

Once a clock in has been processed successfully, steps 806-808, the method 800 records the clock in information in the database of the information processor 102, in one or more implementations. This can include recording care configuration parameters and permissions such as identification information concerning the caregiver, patient or visit, the version of the mobile app used to clock in a visit, the location services data associated with the clock in, and timestamps of the clock in time. An example list of such care configuration items is shown below in Table 4.

TABLE 4

| Parameter Name | Description |
| --- | --- |
| CaregiverID | HHA Caregiver ID |
| VisitID | HHA Visit ID |
| VisitDate | Start date and time of visit |
| PatientID | HHA Patient ID |
| AppVersion | Current version of the app |
| AppInstanceID | Unique App id received after install |
| GPSDistanceInFeet | Distance from patient address when clock out occurred |
| GPSLatitude | Location of phone when clock out occurred |
| GPSLongitude | Location of phone when clock out occurred |
| ConfirmationType | "Punch" |
| LateViolation | "YES" if clock out was after "LateThresholdInMinutes" |
| LateScheduleViolation | "YES" if clock out was after "LateScheduleThresholdInMinutes" |
| GPSAccuracy | InRange, OutOfRange or Unknown |
| SessionUUID | Unique ID for each login session |

In addition to clocking in, the present application contemplates clock out and subsequent timesheet generation practices that additionally implement the facial recognition security techniques described herein. Clocking out completes a visit and, if there are no authorization or permissions issues associated with the time, date, and location of the clock out, permits a user-caregiver with the opportunity to automatically generate a timesheet for submission to a healthcare exchange.

Figure 9:
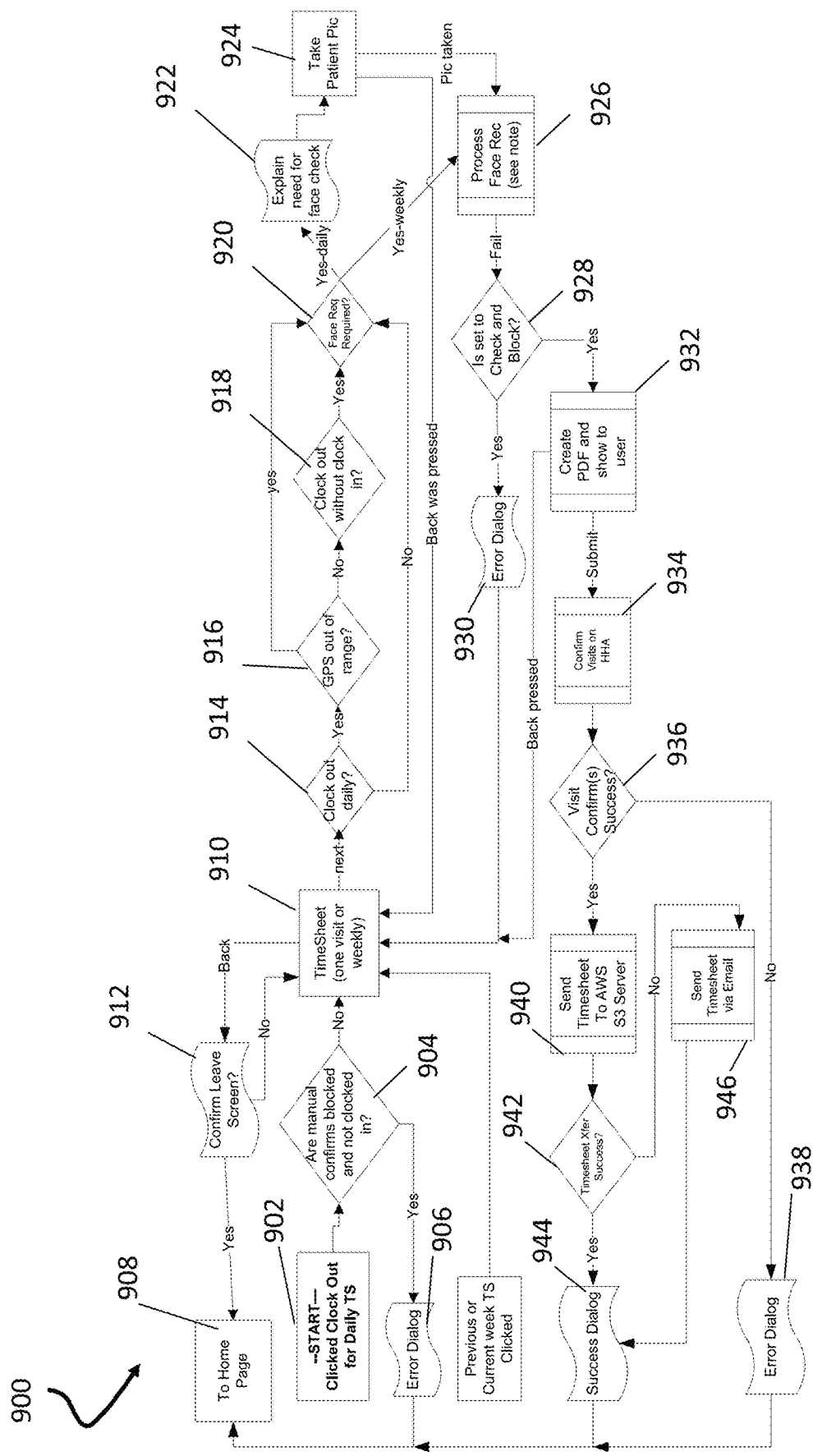
FIG. 9 is a method flow showing example clocking out and timesheet generation processes, in accordance with an implementation of the present application.

With reference now to the flow in FIG. 9, a method 900 is provided for clocking out, generating a timesheet, and transmitting the timesheet to a remote information processor. The method 900 begins by a user selecting the "clock in/out" interactive control from the home screen of the mobile app, step 902. Thereafter, the information processor 102 determines whether there are any permissions associated with the user that block manual confirmation of visits, step 904. In one or more implementations, a manual blocking permission such as this can disallow the user caregiver from performing various actions in certain situations. For example, the user can be prevented from clocking out and confirming a visit if the clock in of the visit was not successfully processed, or if the attempted clock out was part of a visit grouping (e.g., a "weekly visit) that contains additional unconfirmed, non-clocked out visits from the current or previous week. For example, a user permission that is "BlockManualConfig" is evaluated. If BlockManualConfig returns "YES", the user caregiver is shown an error dialog at the user computing device 104, step 906. Thereafter, the method 900 returns the user to the home screen, step 908.

Continuing with the flow of this method 900, in the event that the information processor 102 determines that manual confirmations are not blocked, the method branches to step

910, in which the mobile app at the user computing device determines what time of timesheet to generate—i.e., whether the visit being clocked out is a single visit, or is the last visit scheduled for a work week ("a weekly visit"). Timesheets represent a visit (or visits, in the case of weekly timesheets) by a caregiver to a particular patient. If the user is not prepared to generate a timesheet, he or she may back out by selecting a "back" or "X" button, step 912. In one or more implementations, this generates a prompt asking the user if he or she meant to leave the timesheet screen. If so, the method branches to step 908, displays the home screen and terminates.

Figure 10:
FIG. 10 is the example visit data entry display screen in accordance with an implementation of the present application.

Each generated timesheet has at least one visit and each visit grouping (i.e., more than one associated visits) on the timesheet contains a title with the day and date listed (i.e., Sunday, Dec. 10, 2016) and two date and time entry fields for the start and end time of that visit. In one or more implementations, the date and time entry fields of the visit are editable by a user. For example, the user can select a field by tapping on the displayed entry at the user computing device 104 and set the time or date and time in the date/time dialog that is shown. Each visit section of the timesheet can have one or both date/time fields highlighted in a color, such as yellow. A highlighted field indicates that the respective start or end time was not clocked in or out. The date and time shown in the field is the scheduled time and the user can enter a time to clear the highlight. If the fields are not highlighted (e.g., a normal white background is displayed), the date/time shown is the clocked in or out visit time and is recorded, for example, in a database at the information processor 102. Example time/day visit sections for timesheets are illustrated by FIG. 10. The leftmost example indicates a visit that has been clocked in but not clocked out. The middle example is a visit that was neither clocked in nor clocked out. If the visit actually occurred, the user must check the visit, then enter the actual visit start and end time (the fields currently show the scheduled times). The example on the right illustrates a last visit of the week during a visit clock out or a clocked in and out visit in the middle of the week on a "daily" timesheet.

Additionally, for weekly timesheets, the visit entry can include a check box that indicates whether the user has not properly clocked in or out for that particular visit. If a visit was never checked in or out, it will show in the weekly timesheet as "unchecked" with both fields highlighted in yellow. If the visit should have been clocked in/out but was forgotten, the user can check the box on the weekly timesheet to indicate that the visit actually occurred. Thereafter, the user can manually enter the start and end times. If the visit check box is left unchecked, the app will still allow the timesheet to be submitted but that visit will continue to show as "unconfirmed." In one or more implementations, if a visit check box is checked, but still has highlighted fields, a user is prevented from taking additional photos for facial recognition and timesheet preparation. In one or more implementations, if a facial recognition photo is captured and then visit information is changed in any way, all photos and signatures taken with respect to that visit are cleared from local memory. This is because photos and signatures are preferably captured after all other visit information has been completed and photos/signatures serve as an affirmation that the data associated with the visit is accurate.

Referring back now to FIG. 9, after the user computing device 104 receives a user selection pertaining to generation of a daily timesheet at step 910, the method 900 determines whether a daily visit was selected for clocking out, step 914. Daily visit timesheets are thus those generated for any visit (hourly or live-in) that is not the last visit of the work week. In contrast, as described elsewhere herein, weekly visits are those in which the time period for a caregiver is defined as having multiple visits to the same patient in a week of which time period ends upon the clock out of the last visit of the week or when confirming visits from previous weeks.

If the type of visit is a daily visit, the method 900 implements location based services to confirm the caregiver is in the appropriate patient location to provide care, step 916, as described elsewhere herein. If the method determines that the caregiver and patient are within proximity to one another within a pre-determined tolerance, the method branches to step 920 and implements facial recognition techniques, described herein. If the caregiver and patient cannot be determined to be within proximity of each other, the method determines whether the visit can be clocked out without a clock in, step 918. If so, the method 900 branches to step 920. If not, an error dialog is displayed.

Figure 11B:
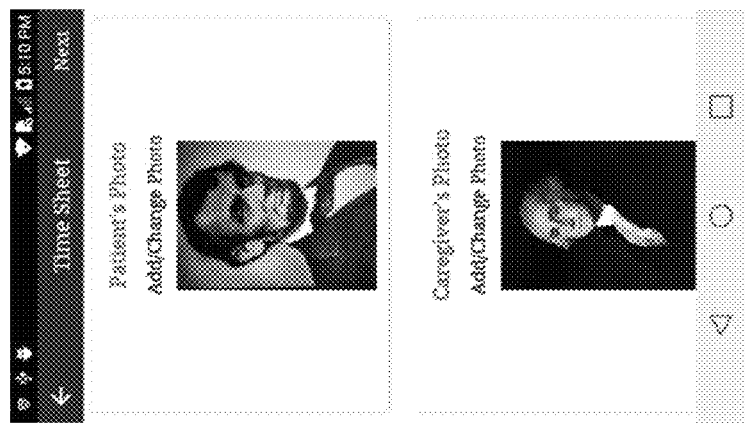
FIG. 11B is an example display screen showing photos added to the mobile app from the display screen of FIG. 11A.
Figure 11A:
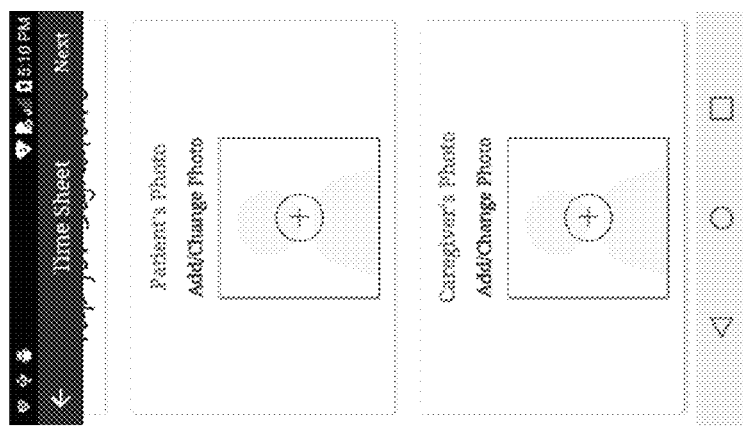
FIG. 11A is an example display screen comprising selectable graphical screen controls for taking or adding a photo of a patient and/or a caregiver, in accordance with an implementation of the present application.
Figure 12:
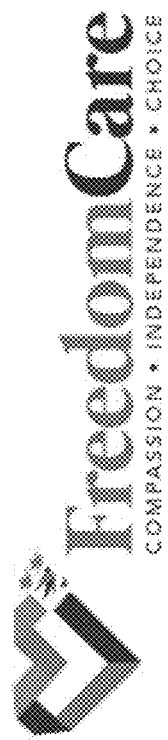
FIG. 12 is an example display screen comprising a generated timesheet for a single daily patient visit, in accordance with an implementation of the present application.
Figure 13:
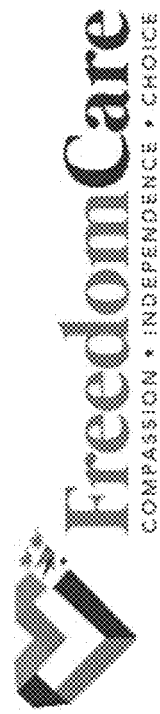
FIG. 13 is an example display screen comprising a generated timesheet for a single daily patient live-in visit, in accordance with an implementation of the present application.

Further to the flow of method 900, at step 920, the method determines whether the permissions associated with the caregiver and/or the patient call for facial recognition. In order to increase security for clocking out, that is, to confirm that the caregiver is indeed the party completing the correct patient visit, facial recognition provides additional security enhancement. If the user desires a clock out for a timesheet for visits that have permissions indicating facial recognition is required, a prompt is optionally displayed explaining the need for facial recognition, step 922. An example screen showing a prompt for patient and caregiver photos for clock out is illustrated by FIG. 11A. Thereafter, one or more photos of the patient and/or caregiver can be taken by the onboard camera of the user computing device 104, step 924. In one or more implementations, the photo taken of the user caregiver upon login can pre-populate the photo prompt if the picture is recent (e.g., within 10 minutes), as illustrated by FIG. 11B. At step 926, the method 900 processes the images taken by the user computing device 104 to perform facial recognition. Facial recognition processing can include reviewing, by a processor, permissions and/or configuration parameters associated with the caregiver, the patient, or both as described herein. In one or more implementations facial recognition is required for both the patient and caregiver for weekly timesheet processing. If the facial recognition fails and the value of a permission associated with the respective party's image being processed (patient or caregiver) is set to block timesheet processing upon a failure, step 928, timesheet processing will stop and an error dialog is displayed on the mobile app, step 930.

If facial recognition successfully validates the caregiver and/or patient for the visit, and the visit is completed, the method 900 then generates a timesheet. A timesheet has patient and caregiver info, the start and end times for the visits of the caregiver/patient combination and contains the signatures and photos. In one or more implementations, the timesheet is sent electronically to the information processor 102 and stored in a database therein. In one or more implementations, the timesheet is also sent electronically to a separate remote backup server. Optionally, the method 900 can include generating a Portable Document Format (PDF) file having the visit information incorporated therein, step 932. In the case of single visit timesheets, a PDF timesheet display only one visit in the table and photos are present only if taken as part of face recognition. The table rows can be color coded based on the GPS location taken at the time the visits were clocked in or out. Exemplary timesheets are shown by FIGS. 12-15.

Referring back to FIG. 9, the method 900 continues thereafter by transmitting the generated timesheet across the communication network to the information processor 102, step 934. Next, the method 900 determines, via a processor at the user computing device 104, whether the timesheets generated have all patient visits confirmed, step 936. In one or more implementations, visits are confirmed at the information processor 102 by verifying the caregiver/patient information matches what is stored at the database of the information processor for the particular visit. For a single visit, the user computing device 104 adjusts the visit information stored at the information processor 102 to contain the new visit end time (the "clock out") and records the GPS location. In one or more implementations, the information processor records whether the caregiver was within the location limit at the time of clocking out. For a weekly timesheet, the user computing device 104 performs this same function for all visit groupings within the weekly visit that are checked on the timesheet and have not already been "confirmed." After a visit is confirmed, in one or more implementations, an API call is made to record information about the visit confirmation, which is recorded at the information processor or other server. Table 5 below displays example parameters for such an API call, such as identification information of the caregiver/patient/visit, the application version of the mobile app used to generate the time sheet, the location services information, whether there were any errors or clock in/out timing violations, and login information.

In addition to the above clock out and timesheet generation methodology, the present application manages clock out scenarios for timesheets differently depending on the type of caregiver visiting a patient. The present application manages clock outs differently for each of two different types of caregivers: (1) "normal" caregivers; and (2) "live-in" caregivers. A normal caregiver is one who visits a patient for a set amount of time and then departs the patient's residence. A live-in caregiver is one in which, for a given patient, at least one of the caregiver's visits is equal or greater than 24 hours long. Live-in caregivers require extra processing in the timesheet to answer questions centered on breaks and being on call. Because of this, there are four different clock out scenarios the above methodology is applicable for: (1) single visit; (2) single visit—live-in; (3) a weekly visit timesheet having multiple visits; and (4) weekly visit timesheet having multiple visits—live-in.

Figure 16C:
FIG. 16C is an example display screen further comprising the timesheet status of the example single daily patient visit of FIG. 16A, in accordance with an implementation of the present application.
Figure 16B:
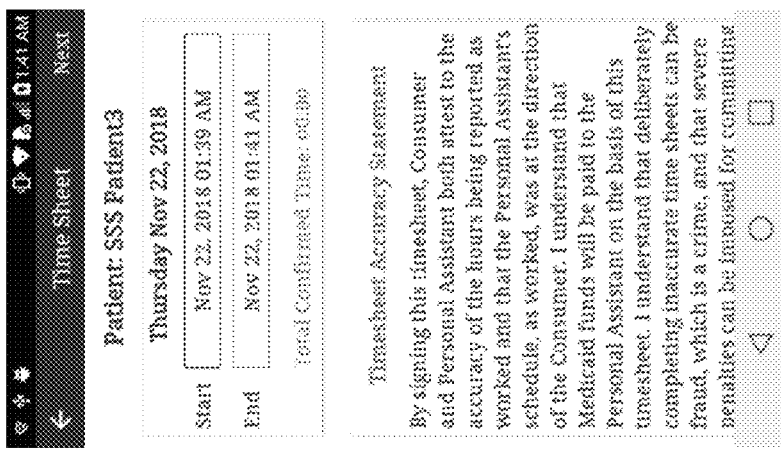
FIG. 16B is an example display screen comprising the clock in or clock out and timesheet status of the example single daily patient visit of FIG. 16A, in accordance with an implementation of the present application.
Figure 16A:
FIG. 16A is an example display screen comprising the clock in/clock out status of an example selectable single daily patient visit, in accordance with an implementation of the present application.

In the first clock out scenario, a single visit clock out covers scenarios in which a user clocks out of a visit that is not the last visit of the week. FIGS. 16A-16C show example single visit clock out display screens. FIG. 16A displays a list of all visits for a selected day, whether they have been clocked in or not. In the example implementation, a clocked in visit displays the start time as "Confirmed In" and the end time as "Scheduled Out". When the caregiver ends a visit, the corresponding timesheet page is shown for a single visit, as in FIGS. 16B and 16C. To clock out a single visit, the user needs to capture the caregiver signature and the signature of the patient, as well as any corresponding required photos for facial recognition processing.

TABLE 5

| Parameter Name | Description |
| --- | --- |
| CaregiverID | HHA Caregiver ID |
| VisitID | HHA Visit ID |
| VisitDate | Start date and time of visit |
| PatientID | HHA Patient ID |
| AppVersion | Current version of the app |
| AppInstanceID | Unique App id received after install |
| GPSDistanceInFeet | Distance from patient address when clock out occurred |
| GPSLatitude | Location of phone when clock out occurred |
| GPSLongitude | Location of phone when clock out occurred |
| MidShiftGPSDistanceInFeet | Mid shift distance away from patient address |
| MidShiftGPSLatitude | Mid shift position latitude |
| MidShiftGPSLongitude | Mid shift position longitude |
| MidShiftDate | Date and time mid shift position was recorded |
| ConfirmationType | "Punch", "CurrentWeekTS" or "PriorWeekTS" |
| LateViolation | "YES" if clock out was after "LateThresholdInMinutes" |
| MidShiftOutOfLocationWindowViolation | "YES" if mid shift location outside "GPSToleranceInFeet" |
| LateScheduleViolation | "YES" if clock out was after "LateScheduleThresholdInMinutes" |
| GPSAccuracy | InRange, OutOfRange or Unknown |
| SessionUUID | Unique ID for each login session |

If confirmation of the visits in the submitted timesheet fails, an error dialog is displayed at the user computing device 104, step 938. If confirmation of the visits in the timesheet succeeds, the method 900 branches to step 940 and the user computing device 104 transmits the PDF version of the timesheet to a remote server. Thereafter, the method determines whether the timesheet transfer was a success, step 942. If so, a success dialog is displayed at the user computing device, step 944. If the app experiences any issues sending the PDF file to the remote server, the user computing device instead sends the PDF file using email, step 946. In one or more implementations, the mobile app will request the user to confirm the sending of the email.

Figures 17A, 17B, 17C:
FIG. 17A is an example display screen comprising the clock in/clock out status of an example single daily patient live-in visit, in accordance with an implementation of the present application.
FIG. 17B is an example display screen comprising questions related to the timesheet status of the example single daily patient live-in visit of FIG. 17A, in accordance with an implementation of the present application.
FIG. 17C is an example display screen further comprising additional questions related to the timesheet status of the example single daily patient live-in visit of FIG. 17A, in accordance with an implementation of the present application.

In a second clock out scenario, a single visit "live-in" clock out is similar to the single visit clock out above, as one visit grouping is displayed to the user initially. An example visit grouping for a live-in clock out is illustrated by FIG. 17A. However, as live-in visits include caregivers who provide care to a patient for a long period of time (>24 hours usually), the mobile app at the user computing device 104 requires the user to answer additional conformance questions prior to timesheet submission. The example display screens of FIGS. 17B and 17C illustrate additional conformance questions. Such questions can be related to whether or not the caregiver received required breaks and did not work more than 13 hours. If the answers provided do not match the predetermined criteria hardcoded by the app (e.g., to not work more than 13 hours), in one or more implementations, a dialog is displayed at the user computing device indicating the caregiver is required to communicate with their coordinator before submitting the timesheet. Default permission values can include, for example, answering yes to working over 13 hours, the caregiver not receiving all required breaks, or yes to remaining on-call during off-hours.

Figure 18C:
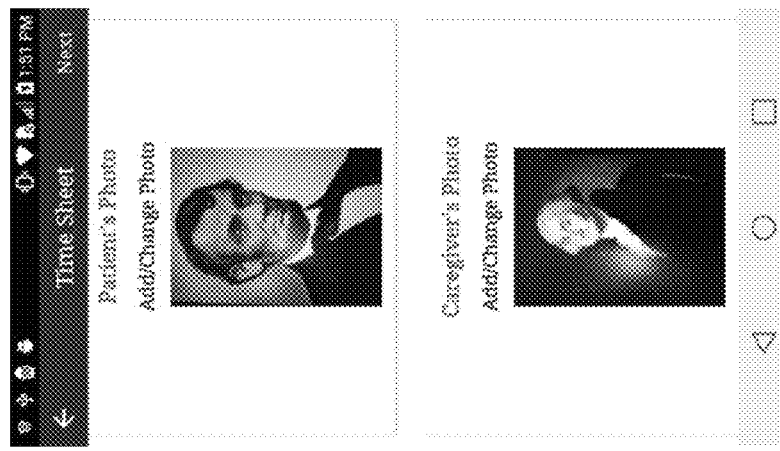
FIG. 18C is an example display screen further comprising the photos added for confirmation of the example weekly patient visit of FIG. 18A, in accordance with an implementation of the present application.
Figure 18B:
FIG. 18B is an example display screen comprising the patient and caregiver signature status of the example weekly patient visit of FIG. 18A, in accordance with an implementation of the present application.
Figure 18A:
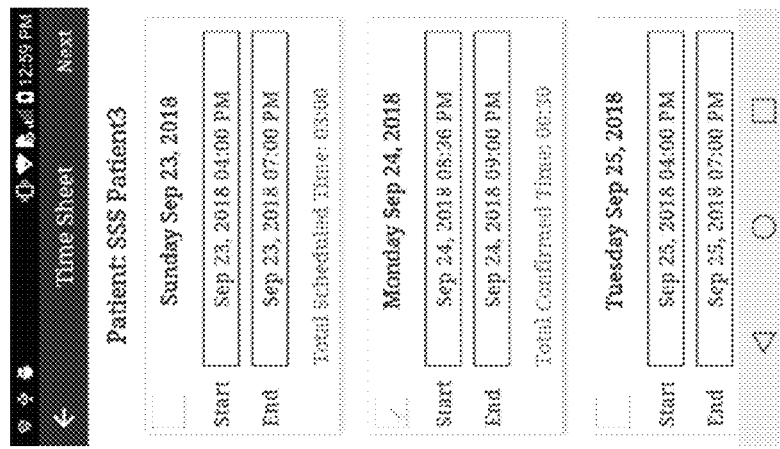
FIG. 18A is an example display screen comprising the clock in/clock out status of an example weekly daily patient visit, in accordance with an implementation of the present application.

In a third clock out scenario, in one or more implementations, multiple visits between the same caregiver and patient can be grouped for submission on a timesheet as a "weekly" visit timesheet. At the end of a visit period, upon selecting a clock out object at the mobile app, each visit made during the visit period is displayed to the user, along with a status indicator as to whether the visit is confirmed (i.e., ready to be processed into a timesheet) or unconfirmed (i.e., needs further user attention). An example display screen showing visits over a weekly visit period is illustrated by FIG. 18A. In this example, the middle visit has been confirmed as lasting the requisite time period (30 minutes), and the top and bottom patient visits are awaiting confirmation by the user that they have been completed. Once all visits in work week are marked as confirmed, the user can generate the time sheet by approving the caregiver and patient identities and submitting the visits for timesheet generation. This can be done using signature and photo facial recognition techniques as described elsewhere herein. Example display screens showing caregiver and patient verification are illustrated as FIGS. 18B and 18C.

Figure 19A:
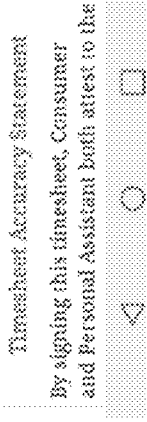
FIG. 19A is an example display screen comprising questions related to the timesheet status of an example weekly patient live-in visit, in accordance with an implementation of the present application.
Figure 19B:
FIG. 19B is an example display screen comprising additional questions related to the timesheet status of the example weekly patient live-in visit of FIG. 19A, in accordance with an implementation of the present application.

In the fourth clock out scenario, in one or more implementations, continuous patient visits that span time periods of greater than a day (i.e., "live-in" care) can be reviewed for submission as a timesheet. For example, a caregiver that provides continuous live-in care to a patient may elect to submit timesheets on a weekly basis—e.g., when the last visit in a work week is completed. Live-in weekly clock outs are similar to the last visit clock out of a normal caregiver, except that additional questions are provided for user response to confirm that the caregiver was indeed providing care continuously throughout the visit period. In one or more implementations, the questions can be answered by the user on a scale basis. For example, the questions can include asking the user how many days of more than thirteen hours the caregiver worked during the period, how many personal assistant breaks occurred, and how many days was the caregiver "on call" (available outside the scheduled hours period). Example display screens for such questions are illustrated by FIGS. 19A and 19B. In these examples, the questions are asked in the form "Indicate the number of days . . . " and the caregiver can tap any of the number squares from 0 to 7 for each question. Like the single visit live in timesheet, if the user answers any of these three questions with anything other than "0", the mobile app displays a dialog noting the need for the caregiver to contact their coordinator and that the timesheet cannot be submitted.

The present application additionally contemplates mobile app functionality in which the secure authorization methodology described herein is applied to updating and modifying future scheduled visits and related schedule information. In one or more implementations, the mobile app includes interactive selectable graphical controls displayed at the home screen for retrieving and modifying a patient's schedule. For example, a control named "Update Schedule" can present a list of future visits for a particular patient. In one or more implementations, for updating visits, the user can only change the visit start and end times so long as the end time is more than a prescribed amount past the start time, as identified by one or more configuration items (e.g., the end time must be at least 15 minutes later than the start time). An additional exemplary control named "Add Visit" can present an interactive interface for the user to add a new visit for a particular patient. For new visits, the user selects the date when the visit starts and selects the start and end times. The available times can be presented in incremental values—e.g., increments of 15 minutes. Upon selecting a particular visit, additional controls can be presented to the user. An exemplary control named "Delete Visit" can present an interactive interface for the user to delete an existing visit for a particular patient. An exemplary control named "Update Visit" presents an interactive interface for the user to update an existing visit for a particular patient. These interactions are accompanied by prompts to confirm selections in one or more implementations. Example display screens illustrating such interactive controls are provided as FIGS. 20A-20D.

The above schedule modification aspects are subject to compliance with caregiver/patient authorization records. Authorization records set limitations as to how, when and who is involved with particular visits. For example, an authorization record can set forth the hours a caregiver may see a patient for during a visit, or across multiple visits. The available hours can be broken down into daily, weekly and overall available hours. The available caregiver hours in an authorization record can be set by outside contract, such by the amount of hours insurance provides for. An individual patient can have one or more authorizations assigned to him or her in the case of a patient having multiple caregivers. In one or more implementations, authorization records are stored at a database at a remote server—e.g., information processor 102. In one or more implementations, authorization records are retrieved upon user selection of an interactive control from the home screen of the mobile app. For example, when a user selects an "Update Schedule" control from the home screen, then selects patient, the mobile app will retrieve all active authorizations for the selected patients.

In one or more implementations, the mobile app confirms that authorization records are associated with particular visits via an API call. The API call can include, for example, field calls to confirmation items concerning contract information (e.g., "ContractID") and caregiver service to be provided (e.g., "ServiceCode"). When a user selects a patient schedule to modify, (e.g., by selecting an "Update Visit" control), the mobile app retrieves all the visits scheduled for the current work week based on the patient selected and the current work week's date range. An example control selection is illustrated by FIG. 20B. Thereafter, a "Change Visit" screen is displayed, an example of which is illustrated by FIG. 20C. If the user selects an interactive control representing "Add Visit", the mobile app provides entry fields for the new visit. Whenever the user selects a date for the new visit, the new visit is added to the schedule, and the new schedule information is retrieved.

After a patient's schedule has been retrieved, the present application provides functionality for authorizing and verifying new and modified visit information. Verification is performed by matching the configuration items associated with the particular patient with the newly submitted, or modified, visit information. If the changed information is authorized as per the configuration item information, then the visit information will be updated at the user computing device 104 and/or information processor 102. For example, if a patient is only authorized for a certain amount of daily visit hours, and a user attempts to add a visit duration beyond the permitted daily allotment, the added visit will be rejected.

In one or more implementations, the authorization and verification methodology includes three primary steps. First, the user computing device 104 requests the most recent particular patient authorization information from the authorization source (e.g., a database at information processor 102). This can be done via API call to the information processor. The most recent authorization source is identified by calling a configuration item associated with patient authorization restrictions (e.g., "authorizationID") that has the largest value. The largest value indicates the most recently created authorization record for that patient, as the authorization records are sequentially created. Second, once the "newest" authorization record is located, the information processor determines whether there are any configuration items associated with "weekly" patient authorizations, and if so, what the largest value associated with such a configuration item is. For example, a patient can be authorized to receive 30 hours of care a week. Finally, if no configuration item authorization for weekly patient authorizations is present in the authorization records, the information processor determines whether there are any configuration items associated with "daily" patient authorizations. Similarly, if the authorization record for the patient includes a value for daily visits, the largest daily value associated with the record is retrieved (e.g., 8 hours in a day). This authorization methodology is advantageous for authorizing newly added patient visits. If the desire is to authorize updated information relating to a specific patient visit (i.e., not a new visit/new authorization record), the authorization methodology identifies the configuration item associated with the patient visit to be updated, as opposed to finding the largest authorization ID configuration item value. Thereafter, the methodology determines whether the update request is for a weekly or daily visit, as above.

Once it is determined that the visit to be added or updated is within the authorized limits of the records associated with the respective patient, the present application contemplates implementing verification steps prior to adding or updating the visit to the patient's schedule. In this way, the integrity of the patient/caregiver visit relationship is further maintained. In one or more implementations, schedule verification begins by determining whether the new/updated visit information references a visit date that is authorized by the patient's records. For example, if the patient records authorize visits for up to two weeks in the future, and the user attempts to add a visit three weeks in the future, this would fail verification.

Thereafter, schedule verification determines whether the change to visit hours will exceed a maximum daily or weekly authorized hours permitted for the patient. Maximum hours ("Authorized Hours") are calculated by adding all visit hours scheduled for the same day as the new or modified visit to be added that have the same patient authorization record details the selected schedule update to be authorized. Visits that have specific markings in the app made by a care manager indicating that the visit did not happen are known as "missed visits". Missed visits differ from unconfirmed visits because unconfirmed visits include scheduled hours. If the schedule update is for a weekly authorization, the verification process confirms that the number of hours in the new or changed visit added to all other visits in the same work week does not exceed the weekly limit of the authorization. If the schedule update is for a daily authorization, the verification process confirms the number of hours in the new or changed visit to the added "Authorized Hours" do not exceed the daily limit associated with that patient. In one or more implementations, the number of hours in the visit is compared against the authorization's "remaining units" field in the configuration item record associated with the patient. For new visits, the hours of the new visits are compared to the remaining units to confirm that the added hours do not exceed the remaining hours. Similarly, for updating a scheduled visit, the difference between the old hours and new hours is compared for any excess. In one or more implementations, the verification process includes checking whether the added or updated visit information would cause a universal maximum hour patient visit threshold to be exceeded. For example, for hourly caregivers, their total schedule hours for a day, regardless of patient, may be limited to a maximum of 16 for one day. If the remaining units (or the "MaxUnits") associated with the patient is zero, this step is skipped.

Next, the verification process re-calculates the "Authorized Hours" by adding all visit hours scheduled for the same day as the modified visit (skipping "missed visits") that also have the same patient authorization record details the selected schedule update to be authorized. In one or more implementations, if the selected authorization is weekly and the max weekly value of the authorization is less than or equal to a maximum amount permitted for a weekly visit (e.g., 70 hours) and the "Authorized Hours" for the patient is greater than a permitted maximum amount (e.g., 10 hours per day), this is flagged as an error. In one or more implementations, if the selected authorization is weekly and the "Authorized Hours" is greater than a prescribed threshold (e.g., 6 hours) and also greater than a percentage of the maximum weekly authorized hours (e.g., greater than 40% of the maximum hours), this is flagged as a failure. In one or more implementations, if the selected authorization is weekly and the max weekly hours are less than or equal to a maximum threshold (e.g., 84 hours), or if it the authorization is for a daily visit and the max daily units are greater than or equal to a threshold (e.g., 12 hours), then the start and end times of the visit being created or modified are limited (e.g., must have a start time no earlier than 5 am and end time no later than 11 pm).

If any of the above steps in the verification process fail, no schedule modification is made, and an error prompt is displayed at the user computing device. In one or more implementations, the user is returned to the home screen or the update/add visit screen. If the verification process succeeds, then a success prompt can be displayed at the user computing device. In one or more implementations, an affirmation is presented to the user upon verification. For example, the mobile app requests the user to acknowledge a statement attesting to the following: "I attest that this schedule change is being made at the direction of the Consumer." Upon verification, in one or more implementations, the changes to the patient schedule are recorded at the database of the information processor 102. This can be performed via an API call having updates to the relevant configuration items associated with the patient that have been modified. This can include creation of new visit configuration items (e.g., a "VisitID" parameter). A non-exhaustive list of example parameters that can be modified by updating a patient schedule are shown below in Table 6, but include the action to be taken to the patient schedule (e.g., creation/updating/deletion), information associated with the caregiver/patient/visit, previous/current/future schedule time information, patient contract information, the type of authorization, and the amount of caregiver hours authorized and remaining.

TABLE 6

| Parameter | Description |
| --- | --- |
| ChangeType | Either "Create", "Update", "Delete" |
| CaregiverID | HHA Caregiver ID |
| PatientID | HHA Patient ID |
| VisitID | HHA Visit ID |
| PreviousScheduledInDate | Previous start date before update...blank for Create operation |
| PreviousScheduledOutDate | Previous end date before update...blank for a Create operation |
| NewScheduledInDate | New start date after update...blank for Update and Delete operations |
| NewScheduledOutDate | New end date after update...blank for Update and Delete operations |
| ContractID | HHA Contract ID...for update and delete, it is the existing visits contract ID...for create it is the same as the authorization used to verify |
| ServiceCode | HHA Service Code...for update and delete, it is the existing visits contract ID...for create it is the same as the authorization used to verify |
| AuthorizationID | HHA Authorization ID of the authorization used to verify the update |
| AuthorizationNumber | HHA Authorization number of the authorization used to verify the update |
| Period | Type of authorization (weekly or daily) |
| HoursForPeriod | HHA's DailyMaxAuth or WeeklyMaxAuth value |
| RemainingUnits | The "Remaining Units" field of the authorization used to verify the update |
| OriginalPeriodHoursUsed | Weekly total less the visit being edited/created or daily total less the visit being edited/created |

Figure 21:
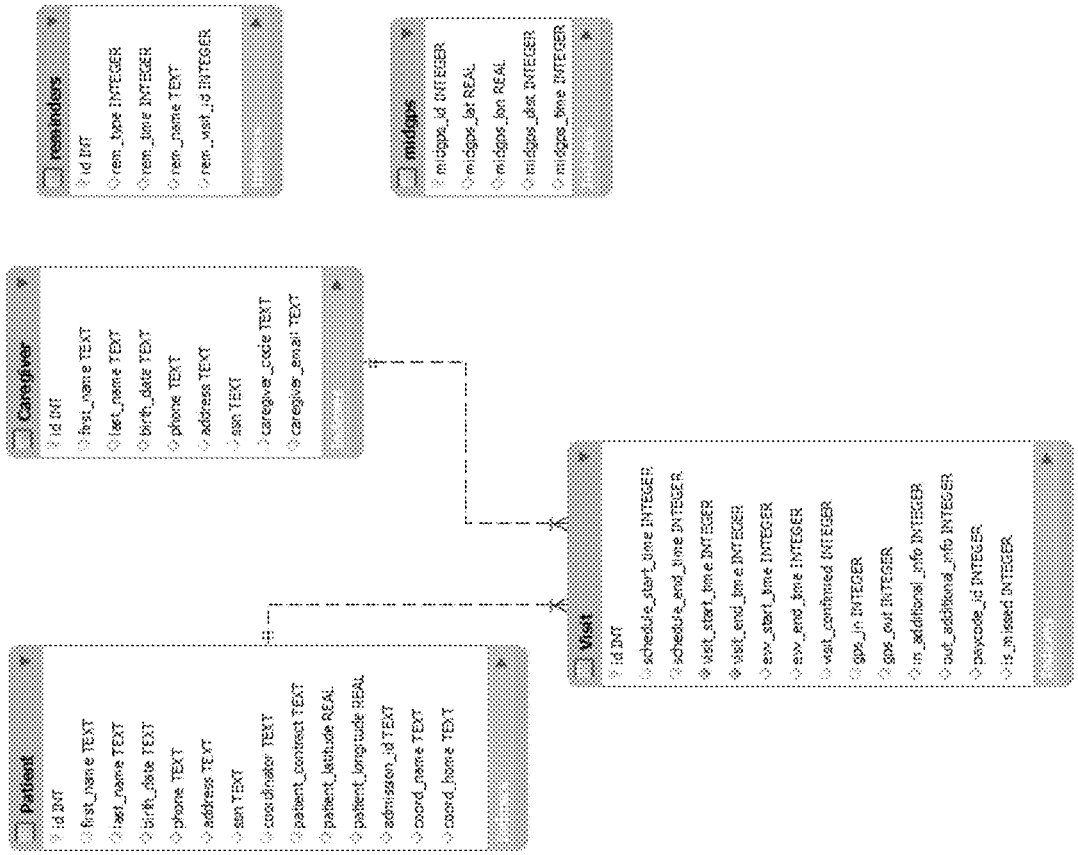
FIG. 21 is an example block diagram illustrating a record layout in connection with an example database implementation of the present application.

FIG. 21 is an example block diagram illustrating a record layout 2100 in connection with an example database implementation of the present application in connection with a patient data source, a caregiver data source, a visit data source and a reminder data source. This database design refers to the SQLite database used on the Android version of the app. The iOS version of the app uses a different, internal memory structure since all information now comes from the network services.

FIGS. 1 through 21 are conceptual illustrations allowing for an explanation of the present invention. Those of skill in the art should understand that various aspects of the implementations of the present invention could be implemented in hardware, firmware, software, or combinations thereof. In such implementations, the various components and/or steps would be implemented in hardware, firmware, and/or software to perform the functions of the present invention. That is, the same piece of hardware, firmware, or module of software could perform one or more of the illustrated blocks (e.g., components or steps).

In software implementations, computer software (e.g., programs or other instructions) and/or data is stored on a machine-readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like.

Notably, the figures and examples above are not meant to limit the scope of the present invention to a single implementation, as other implementations are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific implementations will so fully reveal the general nature of the invention that others can, by applying knowledge within the skill of the relevant art(s) (including the contents of the documents cited and incorporated by reference herein), readily modify and/or adapt for various applications such specific implementations, without undue experimentation, without departing from the general concept of the present invention. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various implementations of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary implementations, but should be defined only in accordance with the following claims and their equivalents.

What is claimed:

1. A computer-based access security method for generating and transmitting a record representing a tracked time expended by a caregiver for services provided to a patient using a user computing device, comprising:
   receiving, by a computing device in response to a selection of a first interactive control provided via a graphical user interface, a clock-in request that includes information representing a current location of the caregiver and representing a current location of the patient;
   verifying, by the computing device, the location of the caregiver and the location of the patient by determining that the received information matches location information stored in a database;
   authorizing, by the computing device, start of care for the patient after the location of the caregiver and the location of the patient is verified;
   receiving, by the computing device in response to a selection of the first interactive control or a second interactive control provided via the graphical user interface, a clock-out request that includes information representing an updated current location of the caregiver and representing an updated current location of the patient;
   verifying, by the computing device, using the updated current location of the caregiver and the updated current location of the patient, that the caregiver and patient are within proximity to one another within a pre-determined tolerance, wherein after the caregiver and patient are verified to be within proximity to one another within the pre-determined tolerance, a photo of the caregiver is captured via a camera at the user computing device;
   collecting and indexing the captured photo to transmit and store the captured photo in a database;
   comparing the captured photo to at least one pre-existing photo stored in the database to validate the caregiver;
   generating, by the computing device, a timesheet after the caregiver is validated; and
   granting access to a user of the user computing device to a remote machine to transmit the timesheet.

2. The method of claim 1, further comprising:
   capturing a location of the caregiver via GPS;
   comparing the captured location to the patient's location to determine whether the captured location is within a pre-determined tolerance; and
   granting access to the remote machine when the captured location is within a pre-determined tolerance.

3. The method of claim 1, further comprising capturing a time and date upon capture of the photo of the caregiver.

4. The method of claim 1, further comprising displaying one or more unread messages to the user of the user computing device upon granting access to the remote machine.

5. The method of claim 1, wherein granting access to the remote machine occurs upon receipt of at least one login credential that includes one or more of a username, a password, a passcode, or a PIN.

6. The computer-based access security method of claim 1, wherein the timesheet is automatically transferred to a remote machine upon generation.

7. The computer-based access security method of claim 1, wherein the step of verifying using the updated current location of the caregiver and the updated current location of the patient occurs after the step of authorizing start of care for the patient.

8. A computer-based access security system for generating and transmitting a record to a database representing a tracked time expended by a caregiver for services provided to a patient, the system comprising:
   a computing device configured by a processor to:
   receive, from a user computing device in response to a selection of a first interactive control provided via a graphical user interface provided on the user computing device, a clock-in request that includes information representing a current location of the caregiver and representing a current location of the patient;
   authorize start of care for the patient after the location of the caregiver and the location of the patient is verified;
   verify the location of the caregiver and the location of the patient by determining that the received information matches location information stored in a database;
   receive, in response to a selection of the first interactive control or a second interactive control provided via the graphical user interface, a clock-out request that includes information representing an updated current location of the caregiver and representing an updated current location of the patient;
   verify, using the updated current location of the caregiver and the updated current location of the patient, that the caregiver and patient are within proximity to one another within a pre-determined tolerance, wherein after the caregiver and patient are verified to be within proximity to one another within the pre-determined tolerance, a photo of the caregiver is captured via a camera at the user computing device;
   collect and index the captured photo to transmit and store the captured photo in the database;
   compare the captured photo to pre-existing photos stored in the database to validate the caregiver;
   generate a timesheet after the caregiver is validated; and
   grant access to the user of the remote machine to transmit the timesheet.

9. The system of claim 8, wherein the user computing device is further configured by the processor to:
   capture a location of the caregiver via GPS;
   compare the captured location to the patient's location to determine whether the captured location is within a pre-determined tolerance; and
   be granted access to the user of the user computing device to the remote machine when the captured location is within a pre-determined tolerance.

10. The system of claim 8, wherein the user computing device is further configured by the processor to capture a time and date upon capture of the photo of the caregiver.

11. The system of claim 8, wherein the user computing device is further configured by the processor to display one or more unread messages to the user of the user computing device upon being granted access to the remote machine.

12. The system of claim 8, wherein access is granted upon receipt of at least one login credential that includes one or more of a username, a password, a passcode, or a PIN.

13. The system of claim 8, wherein the timesheet is automatically transferred to a remote machine upon generation.

14. The system of claim 8, wherein the step of verifying using the updated current location of the caregiver and the updated current location of the patient occurs after the step of authorizing start of care for the patient.

\* \* \* \* \*